United States Patent
Kim et al.

(10) Patent No.: US 7,022,679 B2
(45) Date of Patent: Apr. 4, 2006

(54) PROCESSES FOR THE PREPARATION OF 6-11 BICYCLIC ERYTHROMYCIN DERIVATIVES

(75) Inventors: Heejin Kim, Allston, MA (US); Guoqiang Wang, Belmont, MA (US); Yat Sun Or, Watertown, MA (US); Zhe Wang, Hockessin, DE (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 172 days.

(21) Appl. No.: 10/758,409

(22) Filed: Jan. 14, 2004

(65) Prior Publication Data

US 2004/0171818 A1    Sep. 2, 2004

Related U.S. Application Data

(63) Continuation-in-part of application No. 10/429,485, filed on May 5, 2003, now Pat. No. 6,878,691, which is a continuation-in-part of application No. 10/144,558, filed on May 13, 2002, now abandoned, which is a continuation-in-part of application No. 10/436,622, filed on May 13, 2003, which is a continuation-in-part of application No. 10/144,396, filed on May 13, 2002, now abandoned.

(51) Int. Cl.
*C07H 17/08* (2006.01)

(52) U.S. Cl. .................. 514/29; 536/7.4; 536/18.5
(58) Field of Classification Search ............... 514/29; 536/7.4, 18.5
See application file for complete search history.

(56) References Cited

U.S. PATENT DOCUMENTS

| | | | |
|---|---|---|---|
| 4,990,602 A | 2/1991 | Morimoto et al. | |
| 5,403,923 A | 4/1995 | Kashimura et al. | |
| 5,444,051 A | 8/1995 | Agouridas et al. | |
| 5,527,780 A | 6/1996 | Agouridas et al. | |
| 5,631,355 A | 5/1997 | Asaka et al. | |
| 5,866,549 A | 2/1999 | Or et al. | |
| 5,969,161 A | 10/1999 | Bonnet et al. | |
| 6,046,171 A | 4/2000 | Or et al. | |
| 6,124,269 A | 9/2000 | Phan et al. | |
| 6,399,582 B1 | 6/2002 | Hlasta et al. | |
| 6,645,941 B1 * | 11/2003 | Wang et al. | 514/29 |

FOREIGN PATENT DOCUMENTS

| | | |
|---|---|---|
| WO | WO 00/78773 | 12/2000 |
| WO | WO 01/00582 | 1/2001 |
| WO | WO 01/14397 | 3/2001 |
| WO | WO 01/77134 | 10/2001 |
| WO | WO 03/042228 | 5/2003 |
| WO | WO 03/095466 A1 | 11/2003 |
| WO | WO 03/097659 A1 | 11/2003 |

OTHER PUBLICATIONS

Corey, E.J., Kim C.U., A New and Highly Effective Method for the Oxidation of Primary and Secondary Alcohols to Carbonyl Compounds, Journal of the American Chemical Society, 1972, 94:21, 7586-7587.

* cited by examiner

*Primary Examiner*—James O. Wilson
*Assistant Examiner*—Ganapathy Krishnan
(74) *Attorney, Agent, or Firm*—Elmore, Craig & Vanstone, P.C.; Darlene A. Vanstone; Carolyn S. Elmore

(57) ABSTRACT

The present invention relates to processes and intermediates for the preparation of 6–11 bicyclic erythromycin derivatives. In particular, the present invention relates to processes and intermediates for the preparation of a compound of formula (IX-c):

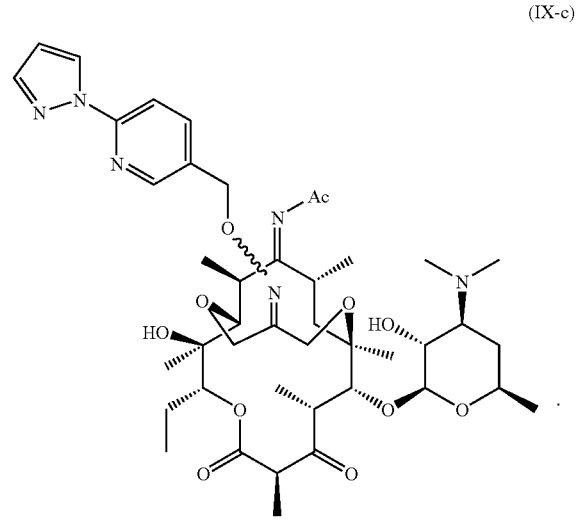

(IX-c)

56 Claims, No Drawings

PROCESSES FOR THE PREPARATION OF 6-11 BICYCLIC ERYTHROMYCIN DERIVATIVES

RELATED APPLICATIONS

This Application is a continuation-in-part of U.S. application Ser. No. 10/429,485, filed May 5, 2003 now U.S Pat. No. 6,878,691, which is continuation-in-part of U.S. application Ser. No. 10/144,558, filed May 13, 2002, now abandoned; and a continuation-in-part of U.S. application Ser. No. 10/436,622, filed May 13, 2003, which is a continuation-in-part of U.S. application Ser. No. 10/144,396, filed May 13, 2002, now abandoned.

TECHNICAL FIELD

The present invention relates to processes and intermediates useful in the preparation of bridged erythromycin derivatives and their respective pharmaceutically acceptable salts.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Macrolides are classified according to the size of the lactone ring (12, 14, 15 or 16 atoms). The macrolide antibiotic family (14-, 15- and 16-membered ring derivatives) shows a wide range of characteristics (antibacterial spectrum, side-effects and bioavailability). Among the commonly used macrolides are erythromycin, clarithromycin, and azithromycin. Macrolides possessing a 3-oxo moiety in place of the 3-cladinose sugar are known as ketolides and have shown enhanced activity towards gram-negative bacteria and macrolide resistant gram-positive bacteria. The search for macrolide compounds which are active against $MLS_B$-resistant strains ($MLS_B$=Macrolides-Lincosamides-type B Streptogramines) has become a major goal, together with retaining the overall profile of the macrolides in terms of stability, tolerance and pharmacokinetics.

SUMMARY OF THE INVENTION

The present invention provides methods for preparing bridged macrocyclic compounds. In one embodiment of the invention, a erythromycin derivative of formula I is reacted with a compound of formula II in the presence of a palladium (0) catalyst. The invention further relates to increasing product yield and decreasing process steps for intermediate and large scale production of bridged macrolides.

DETAILED DESCRIPTION OF THE INVENTION

The processes of the present invention are suitable for synthesizing 6–11 bicyclic erythromycin and ketolide derivatives, or pharmaceutically acceptable salts thereof. In one embodiment, the process comprises the step of reacting a compound of formula (I):

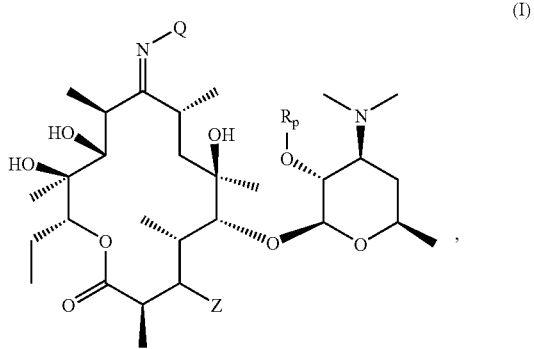

or a pharmaceutically acceptable salt thereof with a compound of formula II:

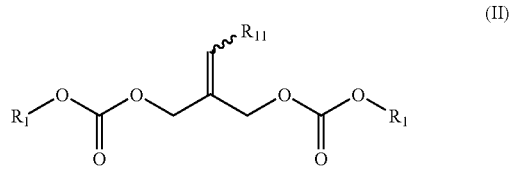

to produce a compound of formula III:

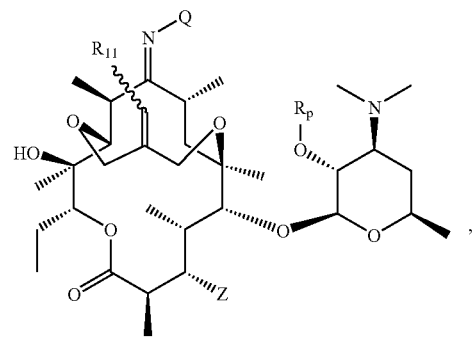

optionally in the presence of a palladium catalyst, wherein,

Each $R_1$ is independently selected from hydrogen, acyl, silane, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group;

Each of $R_3$ and $R_4$ is independently selected from hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group; or can be taken together with the nitrogen atom to which they are attached to form a substituted or unsubstituted heterocyclic or heteroaromatic ring;

Q is independently selected from $R_1$, $OR_1$, or $OC(O)R_1$;

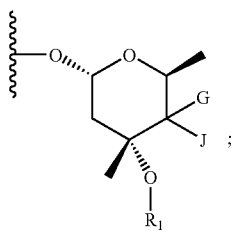

Z is selected from $R_1$, $OR_1$, $OC(O)R_1$, $OC(O)NR_3R_4$, $OS(O)_nR_1$, or one of J or G is hydrogen and the other is selected from $R_1$, $OR_1$, or $NR_3R_4$;

or, J and G, taken together with the carbon atom to which they are attached, are selected from C=O, C=NR$_1$, C=NOR$_1$, C=NO(CH$_2$)$_m$R$_1$, C=NNHR$_1$, C=NNHCOR$_1$, C=NNHCONR$_3$R$_4$, C=NNHS(O)$_n$R$_1$, or C=N—N=CHR$_1$;

$R_{11}$ is independently selected from $R_1$;

$R_p$ is independently selected from $R_1$;

m is an integer; and n is 0, 1, or 2.

Preferred embodiments of the compound of Formula I are the compounds of Formulas I-a and I-b:

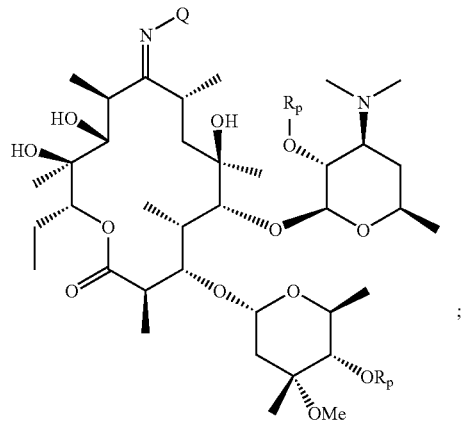

(I-a)

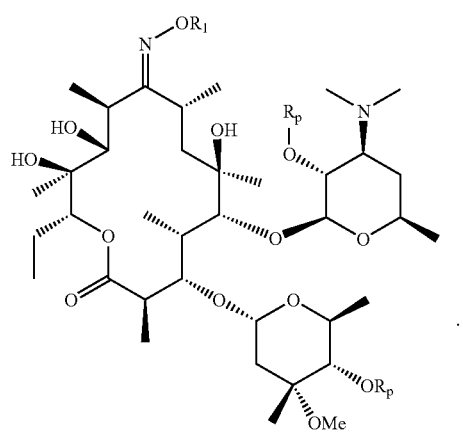

(I-b)

In a most preferred embodiment, the compound of Formula I is a compound of formula (I-c):

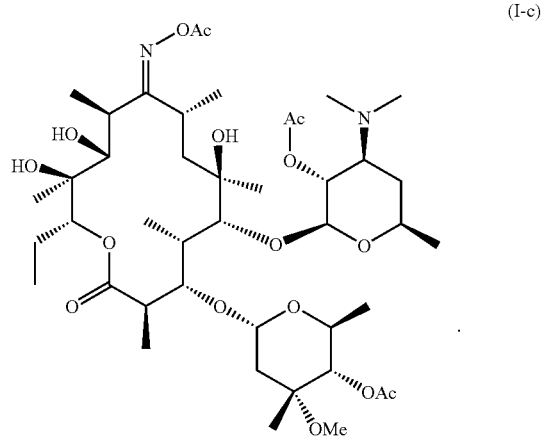

(I-c)

Although compounds of formula I are preferred, other macrocyclic compounds which contain two or more nucleophilic moieties (e.g. —OH, —NH$_2$, —NH—, etc.) may be substituted for the starting material of formula I.

Preferred embodiments of the compound of formula II are compounds wherein $R_{11}$ is hydrogen and/or $R_1$ is tert-butyl.

Compounds of formula (II) that are useful in the preparation of compounds of formula (III), are prepared by the process comprising the step of reacting a compound of formula (II-a):

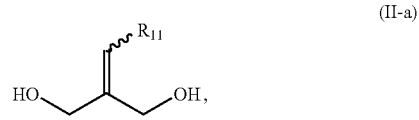

(II-a)

with a C$_1$–C$_6$ alkyl anhydride in the presence of a phase transfer catalyst.

Preferred embodiments of compounds of Formula III include the compounds of Formulas III-a and III-b:

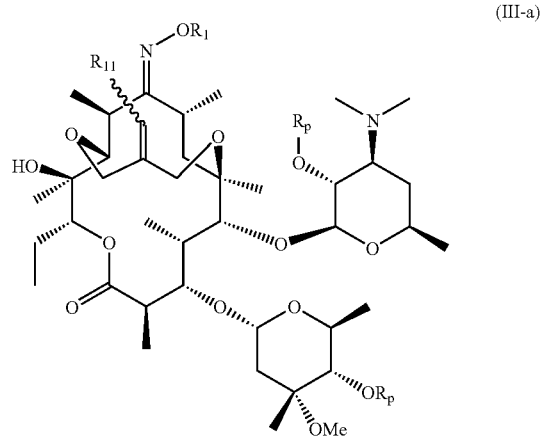

(III-a)

-continued

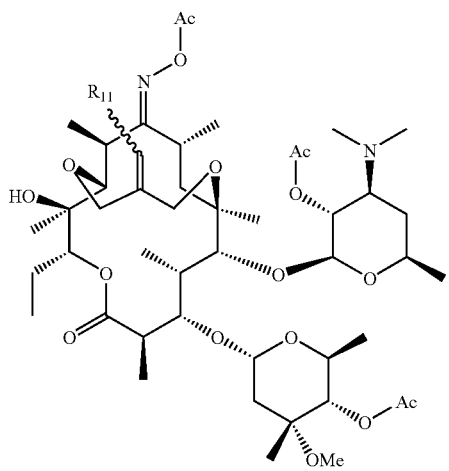

(III-b)

A most preferred embodiment of the compound of Formula III is the compound of Formula III-c:

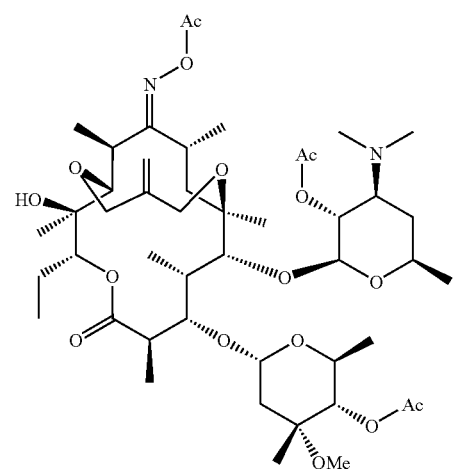

(III-c)

Compounds of formula (III) are useful as intermediates in the preparation of compounds of formula (IV):

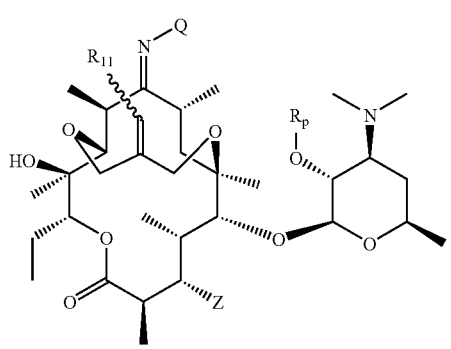

(IV)

Preferred embodiments of the compound of formula IV are compounds of formulas (IV-a) and (IV-b):

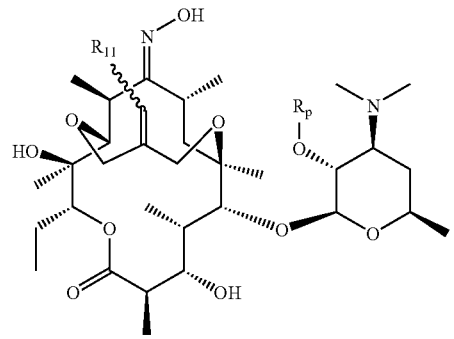

(IV-a)

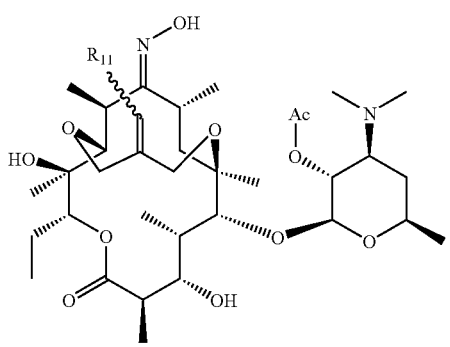

(IV-b)

A most preferred embodiment of the compound of formula (IV) is a compound of formula (IV-c):

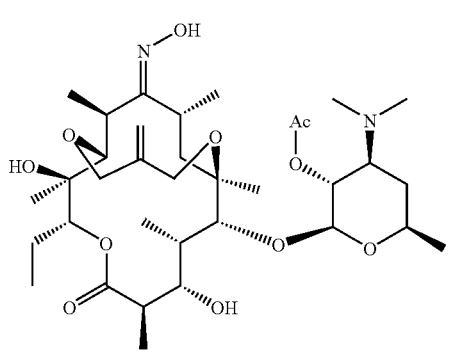

(IV-c)

Another embodiment of the present invention, therefore, is a process comprising the step of hydrolyzing a compound of formula (III) with aqueous acid to provide a compound of formula (IV).

Compounds of formula (IV) are useful as intermediates in preparing compounds of formula (V):

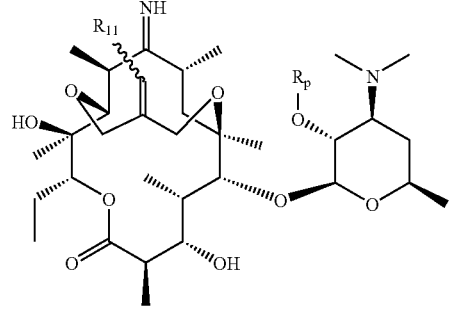

(V)

Preferred embodiments of the compound of formula (V) are compounds of formulas (V-a) and (V-b):

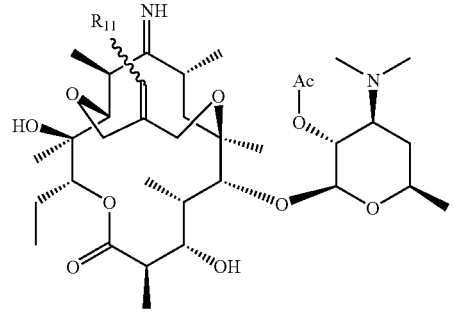
(V-a)

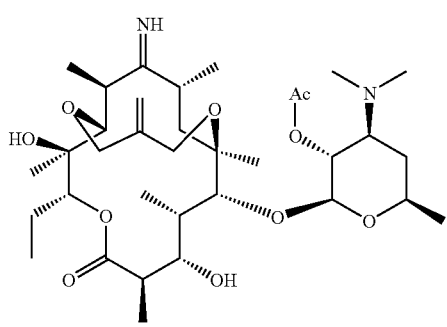
(V-b)

Yet a further embodiment of the present invention, therefore, is a process comprising the step of reducing a compound of formula (IV) with a reducing agent to provide a compound of formula (V).

Compounds of formula (V) are useful as intermediates in the preparation of compounds of formula (VI):

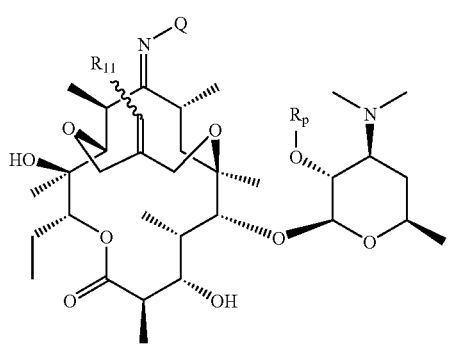
(VI)

Preferred embodiments the compound of formula (VI) are compounds of formula (VI-a) and (VI-b):

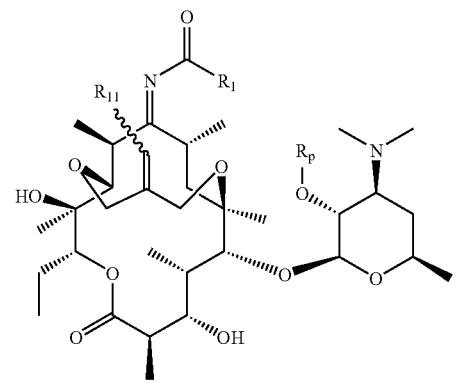
(VI-a)

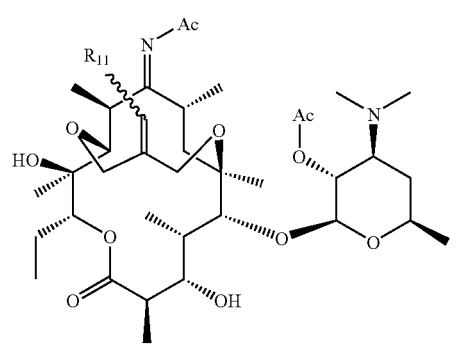
(VI-b)

Yet another embodiment of the present invention, therefore, is a process comprising the step of acylating a compound of formula (V) with an acylating agent to provide a compound of formula (VI).

Compounds of formula (VI) are useful as intermediates in the preparation of compounds of formula (VII):

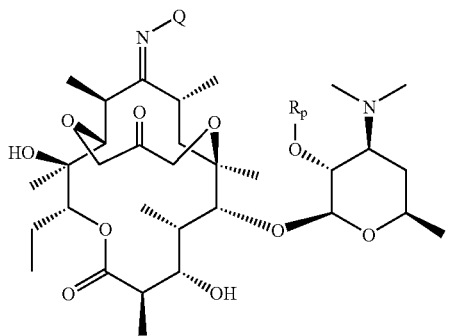
(VII)

Preferred embodiments of the compound of formula (VII) are compounds of formulas (VII-a) and (VII-b):

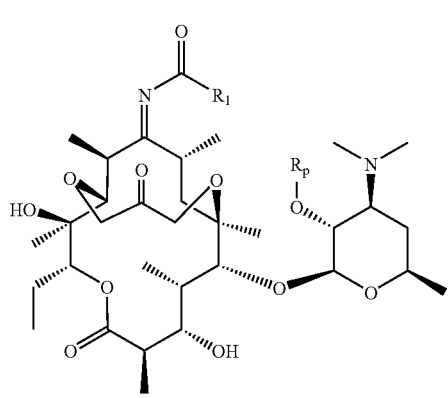 (VII-a)

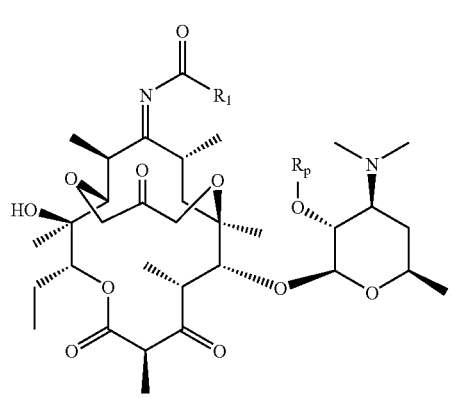 (VIII-a)

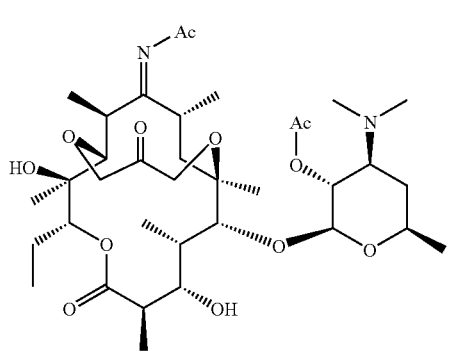 (VII-b)

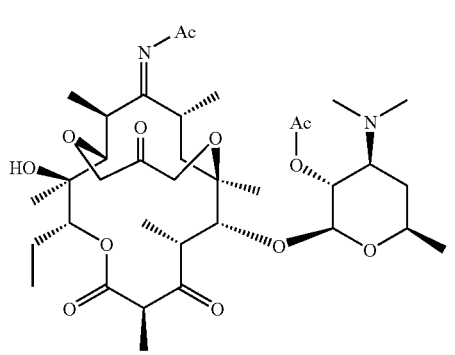 (VIII-b)

Yet a further embodiment of the present invention, therefore, is a process comprising the step of oxidatively cleaving a compound of formula (VI) with a cleaving reagent or reagents which are capable of performing oxidative cleavage to provide a compound of formula (VII).

Compounds of formula (VII) are useful as intermediates in the preparation of compounds of formula (VIII):

Yet another embodiment of the present invention, therefore, is a process which comprises the step of oxidizing a compound of formula (VII) with an oxidizing agent or agents to provide a compound of formula (VIII).

Compounds of formula (VIII) are useful as intermediates in the synthesis of compounds of formula (IX):

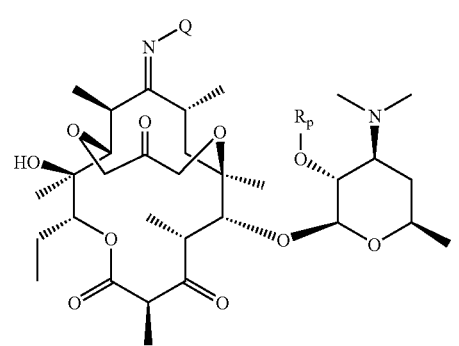 (VIII)

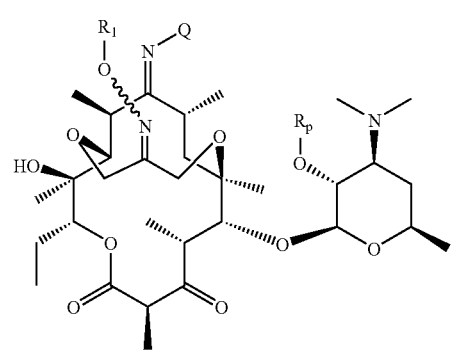 (IX)

Preferred embodiments of the compound of formula (VIII) are compounds of formulas (VIII-a) and (VIII-b):

Preferred embodiments of the compound of formula (VIII) are compounds of formulas (VIII-a) and (VIII-b):

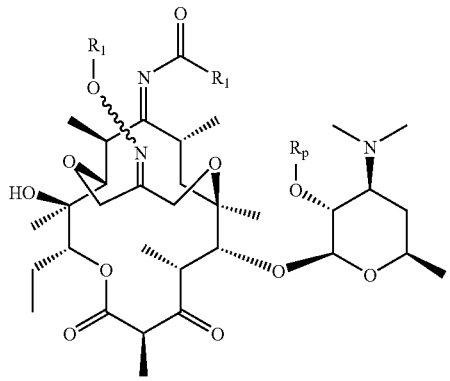

(IX-a)

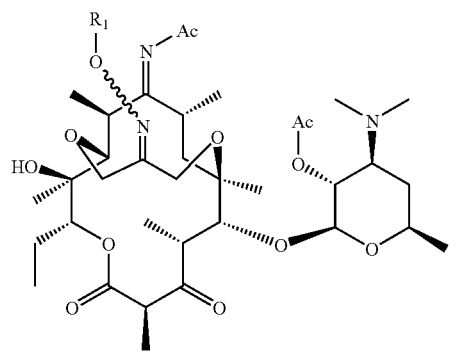

(IX-b)

A most preferred embodiment of the compound of formula (IX) is a compound of formula (IX-c):

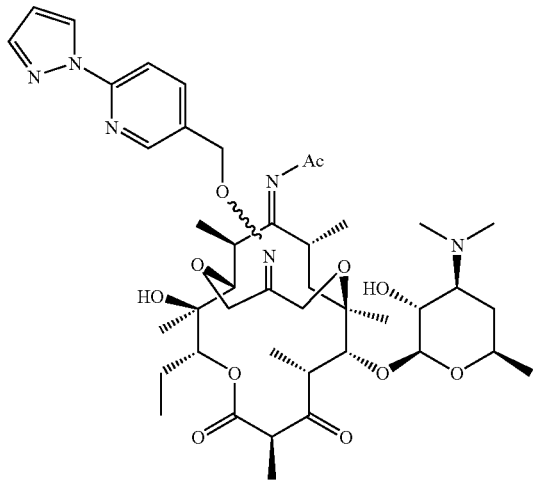

(IX-c)

A further embodiment of the present invention, therefore, is a process which comprises the step of reacting a compound of formula (VIII) with a compound of formula (X): $R_1$—O—$NH_2$(X) to provide a compound of formula (IX). In a preferred embodiment of this process, a compound of formula (VIII) is treated with a compound of formula (XI):

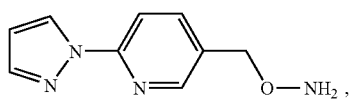

(XI)

to provide a compound of formula (IX-c).

A compound of formula of formula (XI) is a particularly useful intermediate in the process of the present invention and can be prepared by the process comprising the steps of:

a) reacting pyrazole with 6-chloronicotinate in the presence of base, to provide a compound of formula (XI-a):

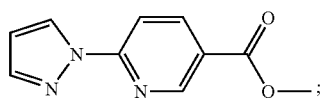

(XI-a)

b) reducing the compound of formula (XI-a) with a reducing agent to provide a compound of formula (XI-b):

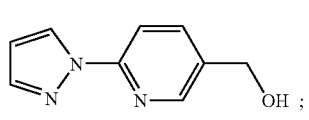

(XI-b)

c) halogenating the compound of formula (XI-b) with a chlorinating reagent to provide a compound of formula (XI-c):

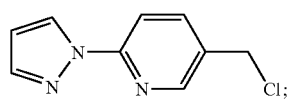

(XI-c)

d) adding N-hydroxyphthalimide or N-hydroxysucinamide to the compound of formula (XI-c) in the presence of a base to provide a compound of formula (XI-d):

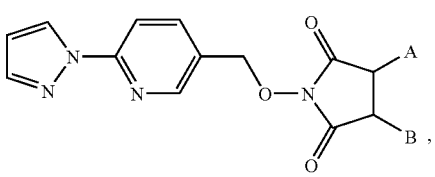

(XI-d)

wherein A and B are each hydrogen or taken together with the carbon to which they are attached to form a cyclic moiety selected from: aryl, substituted aryl, heterocyclic, substituted heterocyclic, alicyclic, or substituted alicyclic; and e) hydrolyzing the compound of formula (XI-d) with a base in a protogenic organic solvent.

Definitions

Listed below are definitions of various terms used to describe this invention. These definitions apply to the terms as they are used throughout this specification and claims, unless otherwise limited in specific instances, either individually or as part of a larger group.

An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

Suitable aliphatic or aromatic substituents include, but are not limited to, —F, —Cl, —Br, —I, —OH, protected hydroxy, aliphatic ethers, aromatic ethers, oxo, —$NO_2$, —CN, —$C_1$–$C_{12}$-alkyl optionally substituted with halogen (such as perhaloalkyls), $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH —$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkynyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkynyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkynyl, —CONH—$C_3$–$C_{12}$-cycloalkyl, —CONH-aryl, —CONH-heteroaryl, —CONH-heterocycloalkyl, —$CO_2$—$C_1$–$C_{12}$-alkyl, —$CO_2$—$C_2$–$C_{12}$-alkenyl, —$CO_2$—$C_2$–$C_{12}$-alkynyl, —$CO_2$—$C_3$–$C_{12}$-cycloalkyl, —$CO_2$-aryl, —$CO_2$-heteroaryl, —$CO_2$-heterocycloalkyl, —$OCO_2$—$C_2$–$C_{12}$-alkyl, —$OCO_2$—$C_2$–$C_{12}$-alkenyl, —$OCO_2$—$C_2$–$C_{12}$-alkynyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkynyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$alkenyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkynyl, —$NHCO_2$—$C_3$–$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$–$C_{12}$-alkyl, —NHC(O)NH—$C_2$–$C_{12}$-alkenyl, —NHC(O)NH—$C_2$–$C_{12}$-alkynyl, —NHC(O)NH—$C_3$–$C_{12}$-cycloalkyl, —NHC(O)NH-aryl, —NHC(O)NH-heteroaryl, —NHC(O)NH-heterocycloalkyl, NHC(S)$NH_2$, NHC(S)NH—$C_1$-$C_{12}$-alkyl, —NHC(S)NH—$C_2$–$C_{12}$-alkenyl, —NHC(S)NH—$C_2$–$C_{12}$-alkynyl, —NHC(S)NH—$C_3$–$C_{12}$-cycloalkyl, —NHC(S) NH-aryl, —NHC(S)NH-heteroaryl, —NHC(S)NH-heterocycloalkyl, —NHC(NH)$NH_2$, NHC(NH)NH—$C_1$–$C_{12}$-alkyl, —NHC(NH)NH—$C_2$–$C_{12}$-alkenyl, —NHC(NH) NH—$C_2$–$C_{12}$-alkynyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC (NH)—$C_2$–$C_{12}$-alkynyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH) NH—$C_2$–$C_{12}$-alkenyl, —C(NH)NH—$C_2$–$C_{12}$-alkynyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkynyl, —S(O)—$C_3$–$C_{12}$-cycloalkyl, —S(O)-aryl, —S(O)-heteroaryl, —S(O)-heterocycloalkyl-$SO_2NH_2$, —$SO_2$NH—$C_1$–$C_{12}$-alkyl, —$SO_2$NH—$C_2$–$C_{12}$-alkenyl, —$SO_2$NH—$C_2$–$C_{12}$-alkynyl, —$SO_2$NH—$C_3$–$C_{12}$-cycloalkyl, —$SO_2$NH-aryl, —$SO_2$NH-heteroaryl, —$SO_2$NH-heterocycloalkyl, —$NHSO_2$—$C_1$–$C_{12}$-alkyl, —$NHSO_2$—$C_2$–$C_{12}$-alkenyl, —$NHSO_2$—$C_2$–$C_{12}$-alkynyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -aryl alkyl, -heteroaryl, -heteroarylalkyl, -heterocycloalkyl, —$C_3$–$C_{12}$-cycloalkyl, polyalkoxyalkyl, polyalkoxy, -methoxymethoxy, -methoxyethoxy, —SH, —S—$C_1$–$C_{12}$-alkyl, —S—$C_2$–$C_{12}$-alkenyl, —S—$C_2$–$C_{12}$-alkynyl, —S—$C_3$–$C_{12}$-cycloalkyl, —S-aryl, —S-heteroaryl, —S-heterocycloalkyl, or methylthiomethyl. It is understood that the aryls, heteroaryls, alkyls and the like can be further substituted.

The terms "$C_2$–$C_{12}$ alkenyl" or "$C_2$–$C_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, alkadienes and the like.

The term "substituted alkenyl," as used herein, refers to a "$C_2$–$C_{12}$ alkenyl" or "$C_2$–$C_6$ alkenyl" group as previously defined, substituted by one, two, three or more aliphatic substituents.

The terms "$C_2$–$C_{12}$ alkynyl" or "$C_2$–$C_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "$C_2$–$C_{12}$ alkynyl" or "$C_2$–$C_6$ alkynyl" group as previously defined, substituted by one, two, three or more aliphatic substituents.

The term "$C_1$–$C_6$ alkoxy," as used herein, refers to a $C_1$–$C_6$ alkyl group, as previously defined, attached to the parent molecular moiety through an oxygen atom. Examples of $C_1$–$C_6$-alkoxy include, but are not limited to, methoxy, ethoxy, propoxy, isopropoxy, n-butoxy, sec-butoxy, tert-butoxy, n-pentoxy, neopentoxy and n-hexoxy.

The terms "halo" and "halogen," as used herein, refer to an atom selected from fluorine, chlorine, bromine and iodine.

The terms "aryl" or "aromatic" as used herein, refer to a mono- or bicyclic carbocyclic ring system having one or two aromatic rings including, but not limited to, phenyl, naphthyl, tetrahydronaphthyl, indanyl, idenyl and the like.

The terms "substituted aryl" or "substituted aromatic," as used herein, refer to an aryl or aromatic group substituted by one, two, three or more aromatic substituents.

The term "arylalkyl," as used herein, refers to an aryl group attached to the parent compound via a $C_1$–$C_3$ alkyl or $C_1$–$C_6$ alkyl residue. Examples include, but are not limited to, benzyl, phenethyl and the like.

The term "substituted arylalkyl," as used herein, refers to an arylalkyl group, as previously defined, substituted by one, two, three or more aromatic substituents.

The terms "heteroaryl" or "heteroaromatic," as used herein, refer to a mono-, bi-, or tri-cyclic aromatic radical or ring having from five to ten ring atoms of which at least one ring atom is selected from S, O and N; zero, one or two ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The heteroaromatic ring may be bonded to the chemical structure through a carbon or hetero atom.

The terms "substituted heteroaryl" or "substituted heteroaromatic," as used herein, refer to a heteroaryl or heteroaromatic group, substituted by one, two, three, or more aromatic substituents.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl.

The term "substituted alicyclic," as used herein, refers to an alicyclic group substituted by one, two, three or more aliphatic substituents.

The term "heterocyclic," as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl.

The term "substituted heterocyclic," as used herein, refers to a heterocyclic group, as previously defined, substituted by one, two, three or more aliphatic substituents.

The term "heteroarylalkyl," as used herein, to an heteroaryl group attached to the parent compound via a $C_1$–$C_3$ alkyl or $C_1$–$C_6$ alkyl residue. Examples include, but are not limited to, pyridinylmethyl, pyrimidinylethyl and the like.

The term "substituted heteroarylalkyl," as used herein, refers to a heteroarylalkyl group, as previously defined, substituted by independent replacement of one, two, or three or more aromatic substituents.

The term "alkylamino" refers to a group having the structure —NH($C_1$–$C_{12}$ alkyl).

The term "dialkylamino" refers to a group having the structure —N($C_1$–$C_{12}$ alkyl) ($C_1$–$C_{12}$ alkyl), where $C_1$–$C_{12}$ alkyl is as previously defined. Examples of dialkylamino are, but not limited to, dimethylamino, diethylarino, methylethylamino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH($C_1$–$C_{12}$ alkyl) or —C(O)N($C_1$–$C_{12}$ alkyl) ($C_1$–$C_{12}$ alkyl), —C(O)NH$_2$, NHC(O)($C_1$–$C_{12}$ alkyl), N($C_1$–$C_{12}$ alkyl)C(O)($C_1$–$C_{12}$ alkyl) and the like.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, *Protective Groups in Organic Synthesis*, 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "protected hydroxy," as used herein, refers to a hydroxy group protected with a hydroxy protecting group, as defined above, including benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis*, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4 th ed., edited by John A. Riddick et al., Vol. II, in the *Techniques of Chemistry Series*, John Wiley & Sons, NY, 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

The term "oxidizing agent(s)," as used herein, refers to reagents useful for oxidizing the 3-hydroxyl of the macrolide ring to the 3-carbonyl. Oxidizing agents suitable in the present process are either Swern oxidation reagents (dimethyl sulfoxide and an electrophilic compound selected from dicyclohexylcarbodiimide, acetic anhydride, trifluoroacetic anhydride, oxalyl chloride, or sulfur trioxide), Dess Martin oxidation reagents, or Corey-Kim oxidation reagents. A preferred method of oxidation is the use of the Corey-Kim oxidation reagents N-chlorosuccinimide-dimethyl sulfide complex.

The term "palladium catalyst," as used herein, refers to optionally supported palladium(0) such as palladium metal, palladium on carbon, palladium on acidic, basic, or neutral alumina, and the like; palladium(0) complexes such as tetrakis(triphenylphosphine)palladium(0) TRIS(DIBENZYLIDENEACETONE)DIPALLADIUM(0); palladium(II) salts such as palladium acetate or palladium chloride; and palladium(II) complexes such as allylpalladium(II) chloride dimer, (1,1'-bis(diphenylphosphino)ferrocene)-dichloropalladium(II), bis(acetato)bis(triphenylphosphine)palladium (II), and bis(acetonitrile)dichloropalladium(II).

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1–19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991); Bundgaard, et al., Journal of Drug Deliver Reviews, 8:1–38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating bacterial infections through administering, pharmaceutically acceptable prodrugs of compounds of the formula I. For example, compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula I. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

Suitable concentrations of reactants is 0.01M to 10M, typically 0.1M to 1M. Suitable temperatures include −10° C. to 250° C., typically −78° C. to 150° C., more typically −78° C. to 100° C., still more typically 0° C. to 100° C. Reaction vessels are preferably made of any material which does not substantial interfere with the reaction. Examples include glass, plastic, and metal. The pressure of the reaction can advantageously be operated at atmospheric pressure. The atmospheres includes, for example, air, for oxygen and water insensitive reactions, or nitrogen or argon, for oxygen or water sensitive reactions.

The term "in situ," as used herein, refers to use of an intermediate in the solvent or solvents in which the intermediate was prepared without removal of the solvent.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which may be used in the descriptions of the scheme and the examples that follow are:

Ac for acetyl;
AIBN for azobisisobutyronitrile;
$Bu_3SnH$ for tributyltin hydride;
CDI for carbonyldiimidazole;
dba for dibenzylidene acetone;
dppb for diphenylphosphino butane or 1,4-bis(diphenylphosphino)butane;
DBU for 1,8-diazabicyclo[5.4.0]undec-7-ene;
DEAD for diethylazodicarboxylate;
DMAP for dimethylaminopyridine;
DMF for dimethyl formamide;
DPPA for diphenylphosphoryl azide;
EtOAc for ethyl acetate;
HPLC for high-pressure liquid chromatography;
MeOH for methanol;
$NaN(TMS)_2$ for sodium bis(trimethylsilyl)amide;
NMMO for N-methylmorpholine N-oxide;
TEA for triethylamine;
THF for tetrahydrofuran;
TPP or $PPh_3$ for triphenylphosphine;
MOM for methoxymethyl;
Boc for t-butoxycarbonyl;
Bz for benzyl;
Ph for phenyl;
POPd for dihydrogen dichlorobis(di-tert-butylphosphinito-κP)palladate(II);
TBS for tert-butyl dimethylsilyl; or
TMS for trimethylsilyl.

All other abbreviations used herein, which are not specifically delineated above, shall be accorded the meaning which one of ordinary skill in the art would attach.

Synthetic Schemes

The present invention will be better understood in connection with Schemes 1–6. It will be readily apparent to one of ordinary skill in the art that the process of the present invention can be practiced by substitution of the appropriate reactants and that the order of the steps themselves can be varied.

Erythromycins can be protected as 9-oximes of formula (I-a) as described in U.S. Pat. Nos. 4,990,602; 4,331,803; 4,680,386; and 4,670,549. Reaction of erythromycin A with hydroxylamine and formic acid in methanol provides a compound of formula (I) wherein Q is OH and Z is

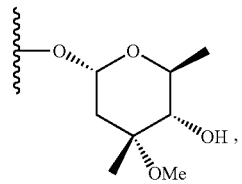

which can be further derivatized without isolation. The preferred amount of hydroxylamine is about 7 to about 10 molar equivalents per molar equivalent of erythromycin A. From about 2 to about 5 molar equivalents of formic acid are used for each molar equivalent of erythromycin A.

The 2'- and 4"-hydroxyl groups as well as the hydroxyl of the 9-oxime of compounds of formula (I-a) can be protected sequentially or simultaneously by reaction with a suitable hydroxyl-protecting reagent in an aprotic solvent, optionally in the presence of catalytic amounts of base, such as DMAP and/or TEA, as described in U.S. Pat. No. 5,892,008, to provide a compound of formula (I-b). Typical hydroxyl-protecting reagents include acetylating agents and silylating agents such as acetyl chloride, acetic anhydride, benzoyl chloride, benzoic anhydride, benzyl chloroformate, hexamethyldisilazane, and trialkylsilyl chlorides. A preferred hydroxyl-protecting reagent of the present invention is acetic anhydride.

Compounds of formula II, useful in the preparation of compounds of formula III, are prepared by treating 2-methylene-1,3-propanediol with di-tert-butyl dicarbonate in an aprotic solvent, in the presence of a phase transfer catalyst (PTC) and an aqueous base. PTCs suitable for the present process include, but are not limited to, tetrabutylammonium bromide, tetrabutylammonium bromide, tetrabutylammonium chloride, tetrabutylammonium fluoride trihydrate, tetrabutylammonium hydrogen sulfate, tetrabutylammonium iodide, tetrabutylammonium thiocyanate, tetrabutylammonium tetrafluoroborate, benzyltetrabutylammonium chloride, and the like; the preferred of which is tetrabutylammonium hydrogen sulfate. In a preferred embodiment of the present conversion, the aprotic solvent is dichloromethane, the aqueous base is 4M to 8M NaOH.

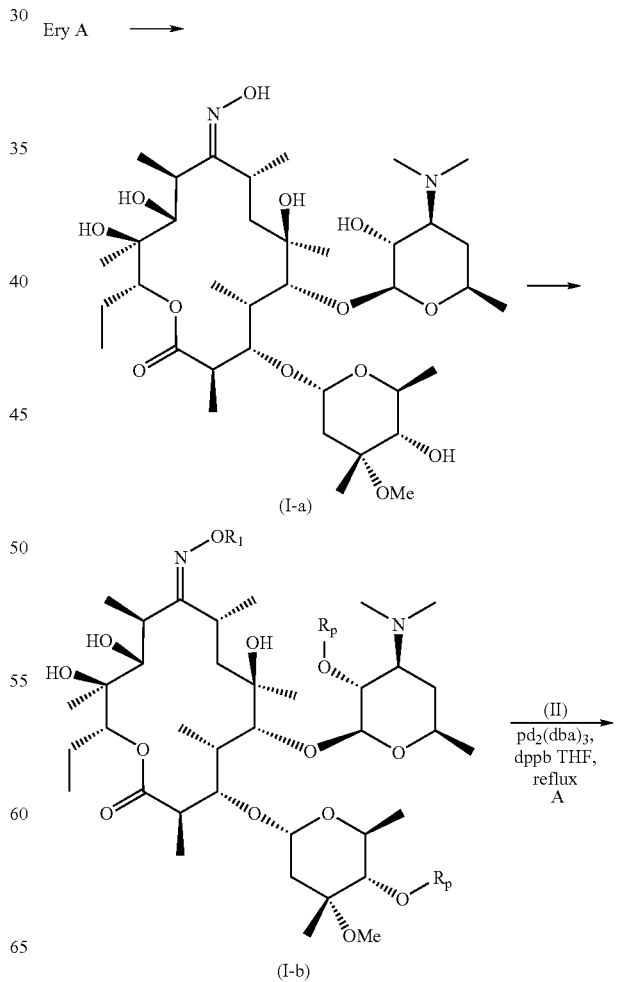

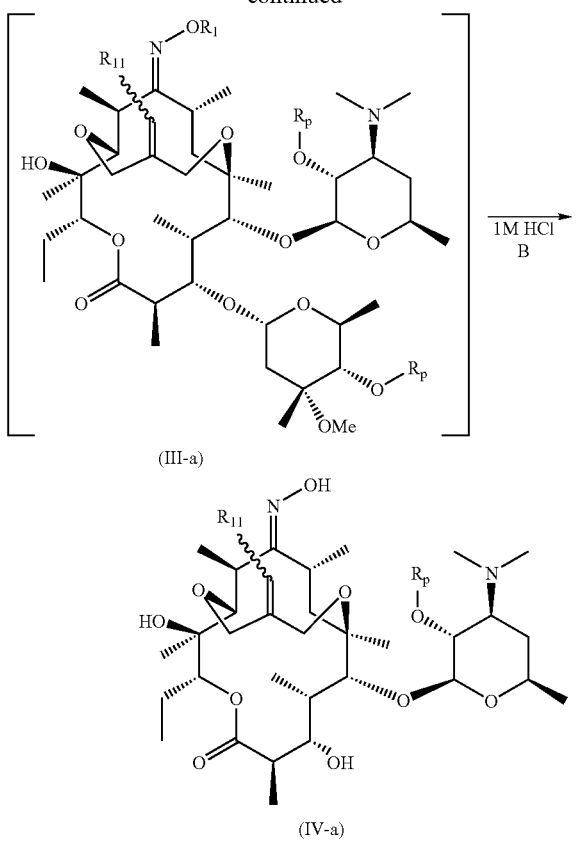

(III-a)

(IV-a)

As illustrated in Scheme 1, step A, erythromycin derivatives of formula (I-b) are converted in the present invention to compounds of formula (III-a) by the treatment of the former with compounds of formula (II):

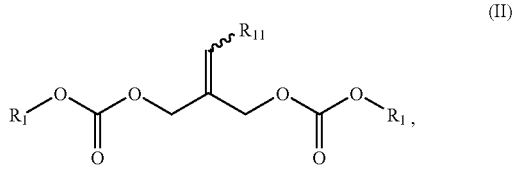

(II)

preferably where $R_1$ is tert-butyl, isopropyl, or isobutyl and $R_{11}$ is hydrogen. In a preferred embodiment, the conversion takes place in an aprotic solvent, at a temperature range of between 30° C. and 100° C., in the presence of a palladium catalyst and an additive for a period of less than about 12 hours.

Alkylation of a compound of formula (I-b) with a compound of formula (II) preferably takes place in the presence of a palladium catalyst. Most palladium (0) catalysts are expected be effective in this process. Some palladium (II) catalysts, such as palladium (II) acetate, which are converted into a palladium (0) species in-situ by a phosphine, will be effective as well. See, for example, Beller et al. *Angew. Chem. Int. Ed. Engl.*, 1995, 34 (17), 1848. A suitable palladium catalyst for this reaction includes, but is not limited to, palladium (II) acetate, tetrakis(triphenylphosphine)palladium (0), tris(dibenzylideneacetone)dipalladium (0) ($Pd_2(dba)_3$), tetradi(benzylideneacetone)dipalladium and the like. Palladium on carbon and palladium (II) halide catalysts are less preferred than other palladium catalysts for this process. A preferred palladium catalyst for this process is a palladium(0) catalyst. A particularly preferred palladium catalyst for this process is $Pd_2(dba)_3$.

In addition, the process is preferably performed in the presence of an additive. Examples of preferred additives include monodentate phosphorus-containing ligands of formulas $P(R_C)_3$ (phosphines) and $P(OR_D)_3$ (phosphites), wherein each $R_C$ is independently hydrogen; alkyl such as methyl, ethyl, and tert-butyl; cycloalkyl such as cyclopropyl and cyclohexyl; optionally substituted aryl, such as phenyl, naphthyl, and ortho-tolyl; and optionally substituted heteroaryl such as furyl and pyridyl; and wherein each $R_D$ is independently alkyl such as methyl, ethyl, and tert-butyl; cycloalkyl, such as cyclopropyl and cyclohexyl; optionally substituted aryl, such as phenyl, naphthyl, and ortho-tolyl; and optionally substituted heteroaryl, such as furyl and pyridyl. Specific examples of additives include, but are not limited to, tri(alkyl)phosphines such as trimethylphosphine, triethylphosphine, tributylphosphine, and the like; tri(cycloalkryl)phosphines such as tricyclopropylphosphine, tricyclohexylphosphine, and the like; tri(aryl)phosphines such as triphenylphosphine, trinaphthylphosphine, and the like; tri(heteroaryl)phosphines such as tri(fury-2-yl)phosphine, tri(pyrid-3-yl)phosphine, and the like; tri(alkyl)phosphites such as trimethylphosphite, triethylphosphite, tributylphosphite, and the like; tri(cycloalkyl)-phosphites such as tricyelopropylphosphite, tricyclohexylphosphite, and the like; tri(aryl)phosphites such as triphenylphosphite, trinaphthylphosphite, and the like; and tri(heteroaryl)phosphites such as tri(fury-2-yl)phosphite, tri(pyrid-3-yl)phosphite, and the like. The term "additive," as used herein, also refers to bidentate phosphines such as 1,4-bis(diphenylphosphino) butane (dppb), 1,2-bis(diphenyl-phosphino)ethane (dppe), 1,1-bis(diphenylphosphino)methane (dppm), 1,2-bis(dimethyl-phosphino)ethane (dmpe), 1,1'-bis(diphenylphosphino)ferrocene (dppf), and the like. A particularly preferred additive of the instant process is 1,4-bis(diphenylphosphino) butane (dppb).

The process is carried out in an aprotic solvent. Suitable aprotic solvents include, but are not limited to, tetrahydrofuran, N,N-dimethylformamide, dimethyl sulfoxide, N-methyl-2-pyrrolidone, hexamethylphosphoric triamide, 1,2-dimethoxyethane, methyl-tert-butyl ether, heptane, acetonitrile, isopropyl acetate and ethyl acetate. Preferred aprotic solvents are tetrahydrofuran or toluene.

The instant conversion is performed preferably at an elevated temperature between 30 and 100° C. A particularly preferred temperature range is between 55° C. and 85° C. A most preferred temperature range for the instant alkylation process is between 60° C. and 75° C.

The instant alkylation process is generally conducted until at least 50% completion, preferably at least about 70% completion, typically until at least 95% completion. Generally, the reaction time will be less than about 12 hours. A preferred reaction time range for the present alkylation process is less than about 8 hours. A most preferred reaction time range for the present alkylation process is less than about 7 hours.

A compound of formula (III-a), wherein $R_6$ and $R_p$ are as previously defined, are converted to a compound of formula (IV-b), wherein $R_p$ is as previously defined, via the process illustrated in Scheme 1, step B. The removal of the cladinose moiety may be achieved either by mild acid hydrolysis or by enzymatic hydrolysis, at a temperature range of between −10° C. and 80° C., for a time period of from 0.5 to 24 hours, to afford a compound of formula (IV-b). Representative acids include dilute hydrochloric acid, sulfuric acid, perchloric acid, chloroacetic acid, dichloroacetic acid or trifluoroacetic acid. Suitable solvents for the reaction include water, methanol, ethanol, isopropanol, butanol and the like. In a preferred embodiment, the removal of the cladinose moiety is achieved by treatment with aqueous hydrochloric acid, for a period of 1 to 2 hours, at a temperature between 50° C. and 70° C. In a most preferred embodiment, 1M aqueous hydrochloric acid is used at a temperature of about 60° C.

organic solvents suitable in this preferred embodiment include, but are not limited to, mixtures of water and methanol, ethanol, isopropanol, or butanol. A particularly preferred protogenic organic solvent for the present conversion is ethanol. The conversion is carried out between 10° C. and 110° C. (preferably between about 20° C. and 50° C.) and over a period of less than about 10 hours (preferably between 2 to 4 hours).

As illustrated in Scheme 2, Step B, compounds of formula (V-a) can be converted to compounds of formula (VI) by

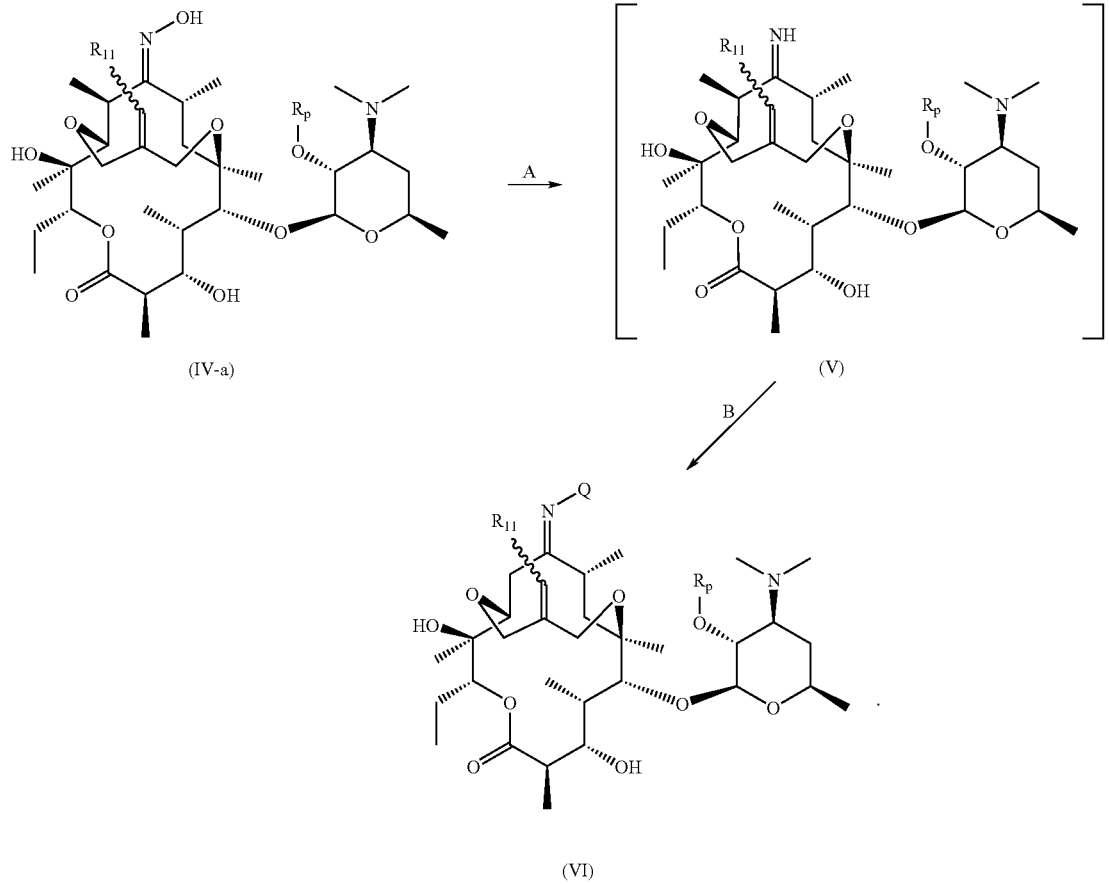

As illustrated in Scheme 2, Step A, conversion of a compound of formula (IV-a) to a compound of formula (V), may be achieved by treating the former with a reducing agent. Reducing agents suitable for this conversion include, but are not limited to, lithium aluminum hydride, titanium (III)chloride, borane, and various sulfides such as sodium hydrogen sulfide and sodium nitrite. For a more detailed account of oxime reduction reaction, see J. March in "Advanced Organic Chemistry" 4$^{th}$ ed., Wiley & Son, Inc, 1992. In a particularly preferred embodiment, a compound of formula (IV-a) is treated with a titanium(III) reducing agent (preferably titanium(III)chloride), under acidic conditions, typically in a protogenic organic solvent. Preferred acids include, but are not limited to, acetic acid, formic acid, dilute hydrochloric acid, dilute phosphoric acid, dilute sulfuric acid, and the like. A particularly preferred acid for the present conversion is aqueous hydrochloric acid. Protogenic treating the former with an acylating agent. In a preferred embodiment, the conversion is carried out in an aprotic solvent. Acylating agents suitable for the instant conversion include, but are not limited to, acetyl chloride, acetic anhydride, benzoyl chloride, benzoic anhydride, and benzyl chloroformate.

Aprotic solvents suitable for the present conversion are dichloromethane, chloroform, tetrahydrofuran, N-methylpyrrolidinone, dimethylsulfoxide, N,N-dimethylformamide, N,N-dimethylacetamide, hexamethylphosphoric triamide, a mixture thereof or a mixture of one of these solvents with ether, tetrahydrofuran, 1,2-dimethoxyethane, 1,2-dichloroethane, acetonitrile, ethyl acetate, acetone, and the like. A preferred aprotic solvent of the present process is selected from dichloromethane, chloroform, N,N-dimethylformamide, tetrahydrofuran, N-methylpyrrolidinone or mixtures thereof. A particularly preferred aprotic solvent is dichloromethane.

Scheme 3

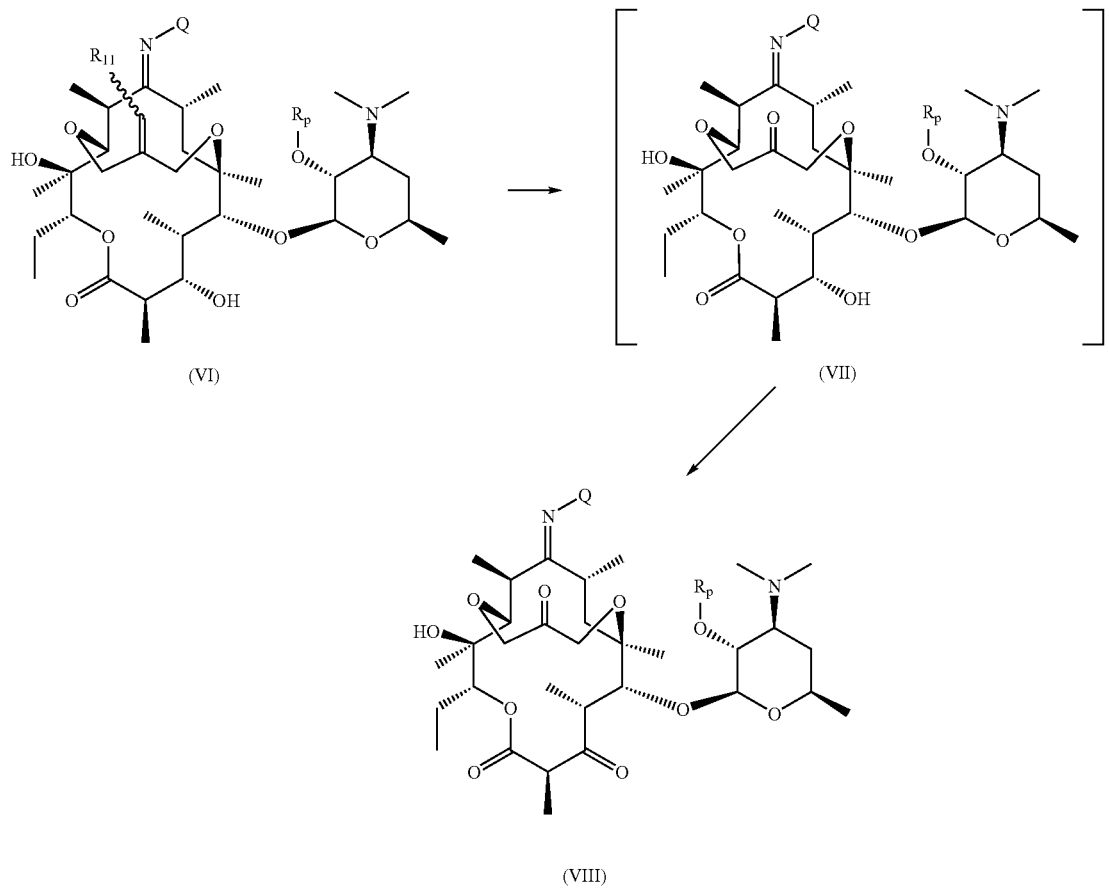

Scheme 3 illustrates the process converting a compound of formula (VI) into a compound of formula (VII) through treatment with a reagent or reagents capable of performing oxidative cleavage. Oxidative cleavage may be performed by, for example, ozonolysis or by treatment with an oxidant followed by a cleaving reagent. Ozonolysis may be achieved by treating the alkene of a compound of formula (VI) with ozone followed by decomposition of the ozonide with the appropriate reducing agent. Suitable reducing agents for this process include, but are not limited to, dimethyl sulfide, zinc, trivalent phosphorous compounds, sodium sulfite, and the like. The reaction is typically carried out in an inert solvent such as, but not limited to, methanol, ethanol, ethyl acetate, glacial acetic acid, chloroform, methylene chloride or hexanes or mixtures thereof, preferably methanol, preferably at about −78° to −20° C. Preferred reducing agents include, but are not limited to, triphenylphosphine, trimethyl phosphite, thiourea, and dimethyl sulfide, preferably triphenylphosphine. A more thorough discussion of ozonolysis and the conditions there for can be found in J. March "Advanced Organic Chemistry" $4^{th}$ ed., Wiley & Son, Inc, 1992.

An alternative method for the preparation of a compound of formula (VII) involves dihydroxylation of a compound of formula (IV) by an oxidant followed by treatment with a cleaving reagent. The glycol is first prepared by reacting alkene with an oxidant. Suitable oxidants for the present process include, but are not limited to, permanganate ion and osmium tetroxide. The process may utilize stochiometric amounts of osmium tetroxide, or, if in the presence of an additional oxidant such as hydrogen peroxide, tert-butyl hydroperoxide, N-methylmorpholine-N-oxide, or barium chlorate only catalytic amounts of osmium tetroxide are necessary. Dihydroxylation reactions can be carried out in a variety of solvents including: 1,4-dioxane, tetrahydrofuran, tert-butanol and diethyl ether, preferably at a temperature of between −15° C. and 15° C.

The resulting glycol can be cleaved by a variety of cleaving reagents including, but not limited to, periodic acid, lead tetraacetate, manganesedioxide, potassium permanganate, sodium metaperiodate, and N-iodosuccinamide. Preferably the cleavage reagent is sodium periodate, the solvent is preferably a mixture of acetone, THF, ethanol, methanol or 1,4-dioxane and water at a temperature of between 0° to 80° C.

A compound of the formula (VII) may be prepared by oxidation of the 3-position alcohol using an oxidizing agent or agents. Oxidizing agents suitable in the present process are either Swern oxidation reagents (dimethyl sulfoxide and an electrophilic compound selected from dicyclohexylcarbodiimide, acetic anhydride, trifluoroacetic anhydride, oxalyl chloride, or sulfur trioxide), Dess-Martin periodane, or Corey-Kim oxidation reagents. A preferred method of oxidation is the use of the Corey-Kim oxidation reagents N-chlorosuccinimide and dimethyl sulfide. The reaction typically takes place in an aprotic solvent at a temperature of between about −78° to 25° C. The reaction time typically is less than 12 hours. A more thorough discussion of the state of the art regarding oxidation of secondary alcohols can be found in J. March in "Advanced Organic Chemistry" 4$^{th}$ ed., Wiley & Son, Inc, 1992.

basic conditions in a variety of solvents. Representative acids include, but are not limited to, hydrochloric, camphorsulfonic acid, phosphoric, sulfuric, para-toluenesulfonic, and pyridinium p-toluene sulfonate. Likewise bases which are useful include, but are not limited to, triethylamine,

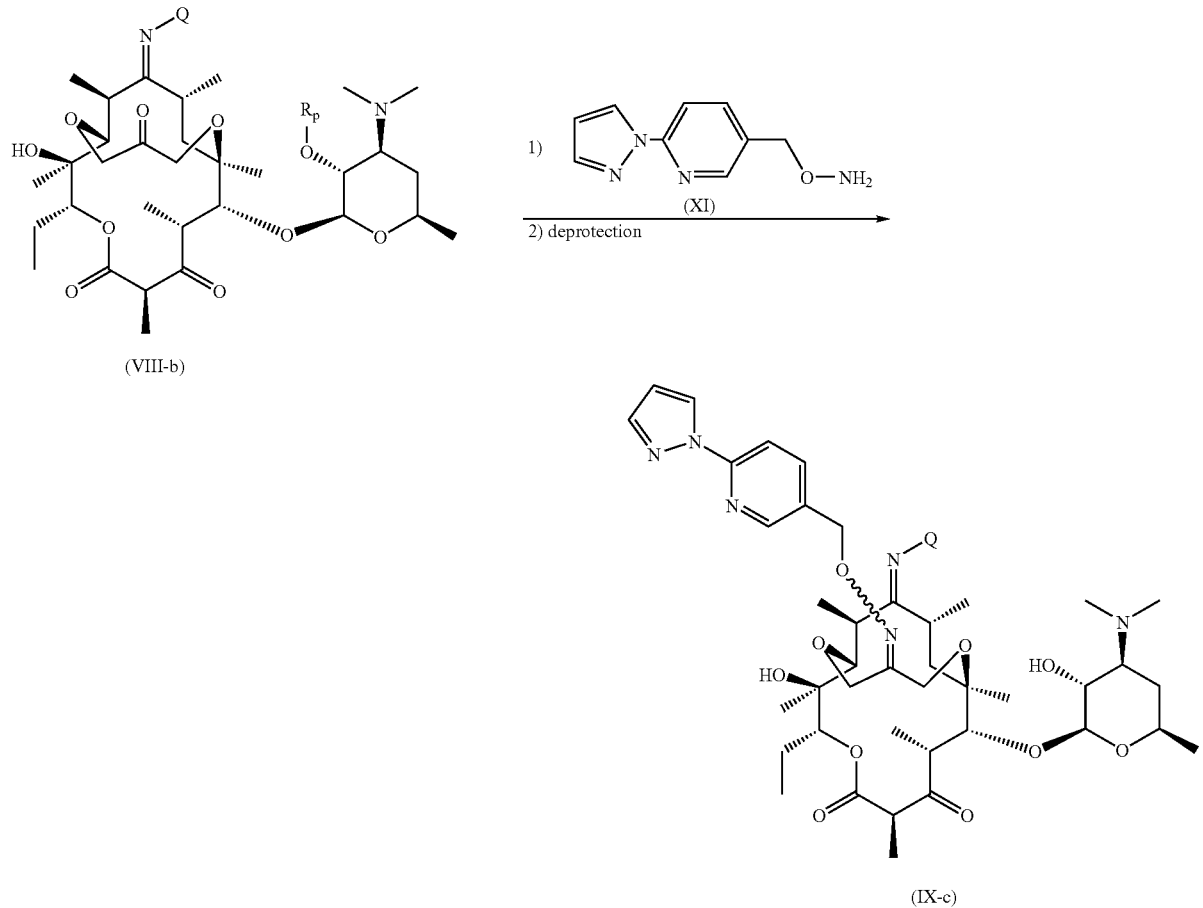

A compound of formula (VIII-b) represents a useful intermediate which can be further functionalized in a variety of ways. Scheme 4 details a procedure for the conversion of a compound of formula (VIII-b) into an oxime compound of formula (IX-c), by first treating with hydroxylamine of formula (XI) followed by deprotection of the 2' hydroxyl. Oxime formation can be accomplished under either acidic or pyridine, diisopropylethyl amine, 1,5-lutidine, imidazole, and the like. Appropriate solvents include, but are not limited to, methanol, ethanol, water, tetrahydrofuran, 1,2-dimethoxyethane, and ethyl acetate. Preferably the reaction is run in ethanol using triethylamine as the base. The reaction temperature is generally 0° C. to 50° C. and the duration of the reaction is less than 12 hours. The deprotection can be achieved by for example methanolysis.

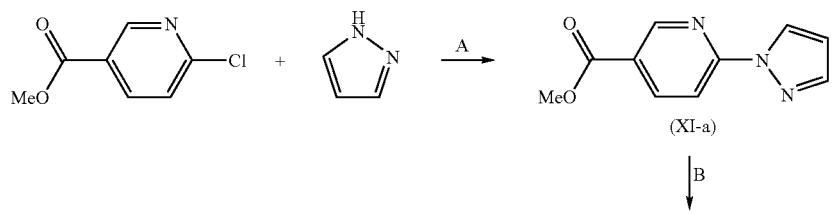

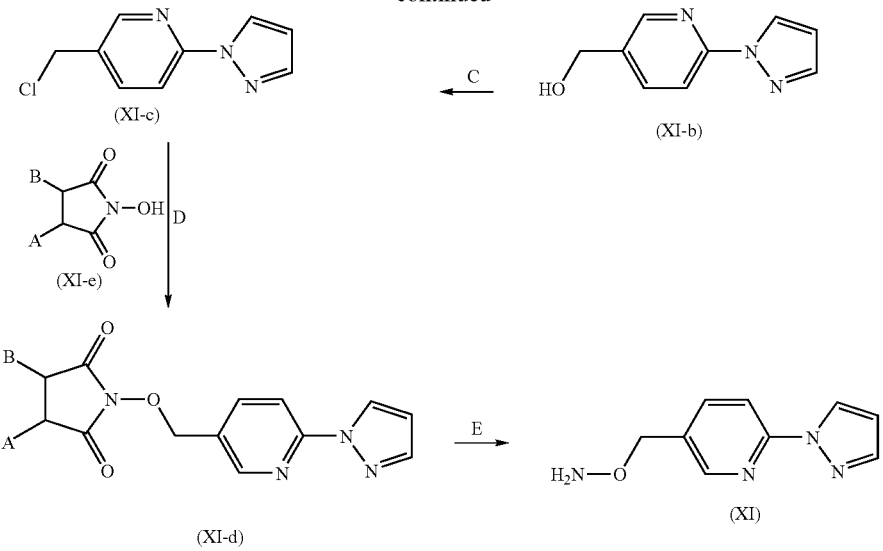

As illustrated in Scheme 5, Step A, a compound of formula XI is prepared by first reacting methyl 6-chloronicotinate with pyrazole in the presence of a base, preferably in an aprotic solvent, to provide a compound of the formula (XI-a). In a preferred embodiment of the instant reaction, the reaction temperature is between 25° C. and 60° C. and the duration of the reaction is less than 6 hours. In a particularly preferred embodiment of the instant reaction, the base is sodium hydride and the aprotic solvent is dimethyl sulfoxide.

A compound of formula (IX-b) is prepared, as illustrated in Step B of Scheme 5, by reducing a compound of formula (IX-a) with a reducing agent. Reducing agents useful in this conversion include, but are not limited to, sodium borohydride, lithium aluminum hydride, and the like. The present reaction preferably takes place in a protogenic organic solvent. Most preferably, the protogenic organic solvent is a mixture of tert-butanol and methanol. Preferably, the reaction is performed at from room temperature to reflux conditions for a duration of less than 10 hours. Most preferably the reaction is performed under reflux conditions for a period of 4 to 6 hours.

A compound of formula (XI-c) is prepared, as illustrated in Step C of Scheme 5, by halogenating compound of formula (XI-b) with a halogenating agent. Halogenating agents suitable for the instant conversion include, but are not limited to, $PBr_3$, thionyl chloride, and the like. The present reaction preferably takes place in an aprotic solvent, at a temperature between about 0° C. and 50° C., for a duration of less than 24 hours. Most preferably the present conversion takes place in methylene chloride, at room temperature, and for a duration of from 12 to 18 hours.

A compound of formula (XI-d) is prepared, as illustrated in Step D of Scheme 5, by adding the compound of formula (XI-e) to a compound of formula (IX-c), wherein A and B are hydrogen or A and B taken together with the carbons to which they are attached form a cyclic moiety selected from aryl, substituted aryl, heterocyclic, substituted heterocyclic, alicyclic, or substituted alicyclic. Preferably A and B are hydrogen or A and B taken together with the carbon atoms to which they are attached are phenyl. The present conversion preferably takes place in the presence of a base in an aprotic solvent.

A compound of formula (XI) is prepared, as illustrated in Step E of Scheme 5, by hydrolyzing the compound of formula (XI-d) with a base in a protogenic organic solvent or an aqueous mixture thereof. Preferably the base is either hydrazine or ammonia.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications bincluding, without limitation, those relating to the chemical structures, substituents, derivatives, formulations and/or methods of the invention may be made without departing from the spirit of the invention and the scope of the appended claims.

Example 1

Preparation of
O-Bis(Boc)-2-Methylene-1,3-Propanediol
(Compound of formula II, wherein $R_{11}$ is hydrogen and $R_1$ is tert-butyl)

To a solution of di-tert-butyl dicarbonate (6.6 kg) in methylene chloride (15.0 L, 15 volumes) was added 2-methylene-1,3-propanediol (1.00 kg) and phase transfer catalyst tetrabutylammonium hydrogensulfate (0.641 kg). The resulting reaction mixture was then agitated vigorously at about 15° C. while adding over a 2 hr period, 6M aqueous sodium hydroxide solution (13.2 L) and controlling the temperature between 25 to 30° C. The resulting two-phase reaction mixture was subsequently agitated for a period of 2–3 hrs at 25° C.

The aqueous layer was discarded and additional phase transfer catalyst tetrabutylammonium hydrogensulfate (0.064 kg, 10% of the initial amount), di-tert-butyl dicarbonate (0.66 kg, 10% of the initial amount), and methylene chloride (2.0 L, 2 volumes) was added to the remaining organic reaction mixture. To the reaction mixture was also added 6M aqueous sodium hydroxide solution (1.32 L, 10% of the initial amount) over a period of about 0.5 to 1 hr, while controlling the temperature between 25 to 30° C. The resulting two-phase reaction mixture was then agitated at about 25° C. for additional 3 to 4 hr. Allowing more than 3 hrs of agitation time is often required to complete the hydrolysis of the excess di-tert-butyl dicarbonate. The aqueous layer was discarded. The resulting organic phase was washed with water (3×8.0 L), diluted with EtOAc (6 L, 6 volumes), and distilled to an oil foam with quantitative yield.

$^1$H (500 MHz, CDCl$_3$) δ 5.15, 4.98, 4.79, 4.68, 4.68, 4.33, 4.31, 3.89, 3.77, 3.67, 3.45, 3.35, 3.19, 2.88, 2.78, 2.74, 2.42, 2.17, 2.11, 2.06, 1.95, 1.72, 1.66, 1.51, 1.48, 1.43, 1.34, 1.27, 1.19, 1.19, 1.18, 1.14, 1.13, 1.11, 0.95, 0.85

Example 2

Preparation of Erythromycin A 9-oxime 9,2',4"-triacetate (Compound of formula (I-c))

To a solution of erythromycin A oxime (1.0 kg) in EtOAc (4 L, 4 volumes) was added TEA (0.744 L) and DMAP (48.9 g). While agitating and maintaining a temperature of less than 40° C., to the resulting reaction mixture was added acetic anhydride (0.441 L) over a period of 1–5 hrs. The reaction mixture was then agitated for an additional 1–5 hr period at about 25° C. Additional TEA (0.0744 L, 10% of initial amount) was then added to the reaction mixture, and subsequently additional acetic anhydride (0.0441 L, 10% of initial amount) was added over the course of 30 min while maintaining a temperature of less than 35° C. This mixture was then further agitated for 1.5–2 hr at about 25° C.

After the reaction had gone to completion, the reaction mixture was diluted with EtOAc (6 volumes), quenched with aqueous NaHCO$_3$ solution 3.0 L (3 volumes), and agitated for 5–10 min at about 25° C. The aqueous phase was then discarded. The remaining organic mixture was washed with aqueous NaHCO$_3$ solution (3.0 L, 3 volumes) and 15% aqueous brine (3.0 L, 3 volumes), and concentrated in vacuo. The concentrated solution was then taken up in acetonitrile (4.0 L, 4 volumes) and concentrated in vacuo two times until crystallization occurs. Upon formation of crystals, the slurry was agitated at 10° C. to 15° C. for at least 2 hr and the crystals were collected and dried under vacuum to afford white crystalline product with a typical yield of 70–80%.

$^1$H (500 MHz, CDCl$_3$) δ 5.15, 4.98, 4.79, 4.68, 4.68, 4.33, 4.31, 3.89, 3.77, 3.67, 3.45, 3.35, 3.19, 2.88, 2.78, 2.74, 2.42, 2.17, 2.11, 2.06, 1.95, 1.72, 1.66, 1.51, 1.48, 1.43, 1.34, 1.27, 1.19, 1.19, 1.18, 1.14, 1.13, 1.11, 0.95, 0.85

$^{13}$C (125 MHz, CDCl$_3$) δ 178.7, 175.4, 170.4, 170.0, 168.3, 100.6, 96.3, 83.4, 79.4, 79.0, 77.4, 74.9, 74.0, 72.6, 72.2, 70.1, 67.7, 63.6, 63.4, 49.5, 45.0, 40.7, 39.2, 37.4, 35.7, 34.5, 31.5, 28.6, 26.8, 21.8, 21.7, 21.5, 21.3, 21.1, 20.0, 18.7, 18.4, 16.7, 16.1, 14.9, 10.9, 9.2

Example 3

Preparation of 6,11-O,O-Bridged Erythromycin A 9-Oxime 9,2',4"-triacetate (Compound of formula (III-c))

To a solution of the title compound of Example 2 (1.00 kg) in anhydrous THF (5.0 L, 5 volumes) was added a solution of the title compound of Example 1 (0.62 kg) in anhydrous THF (2.0 L, 2 volumes) while agitating. The resulting reaction mixture was subsequently degassed twice by application under reduced pressure and placed under nitrogen. To the degassed reaction mixture was added 1,4-bis(diphenylphosphino)butane (dppb) (19.5 g), and tris (dibenzylideneacetone)dipalladium(0) [Pd$_2$(dba)$_3$] (20.8 g), after which the resulting reaction mixture was immediately degassed twice as previously described.

The degassed reaction mixture was then heated, while being agitated, to reflux [typically, reflux begins at about 65° C.] over the period of about 1 to 2 hrs and then held at a temperature of 67° C. to 69° C., while being agitated, for a period of 6 hr. After the 6 hr period, the reaction mixture was allowed to cool to about 25° C. over the period of 2 to 3 hrs and the reaction mixture was analyzed for completion by HPLC.

Once it had been determined that the reaction had gone to completion, the reaction was then filtered through a short pad (about 2 inches thick) of silica gel 0.25–0.5 kg to remove the palladium catalyst, phosphine ligand, and other polar impurities. The reaction vessel was then rinsed with reagent-grade THF (2.0 L, 2 volumes), agitate/wash for 10 min, and filtered through the short pad of silica gel, combining with filtrate from the reaction mixture. The combined filtrate was then concentrated in vacuo to afford the title compound in THF solution. The final remaining volume of the THF solution of the title compound was approximately 2–3 L (2–3 volumes) and was used directly in the following step without isolation.

Example 4

Preparation of 3-Decladinose-6,11-O,O-Bridged Erythromycin A 9-Oxime (Compound of formula (IV-c))

To the concentrated solution of the title compound of Example 3 was added 1M hydrochloric acid solution in water (8.0 L, 8 volumes). The resulting reaction mixture was subsequently agitated and heated to 60° C. over a period of 1–2 hr and then held at said temperature for an additional 2 hr.

After the reaction had gone to completion (determined by HPLC), the reaction mixture was cooled to about 25° C. over the period of about 3 hrs. The aqueous reaction mixture was then washed with methyl tert-butyl ether (MTBE) (4.0 L×2, 4 volumes×2) while agitating at 25° C. for 10 min, keeping the aqueous layer. To the aqueous reaction mixture was then added saturated aqueous K$_2$CO$_3$ solution (about 0.8 kg of solid potassium carbonate in water) at 20 to 30° C. over the period of 1 to 2 hrs until the mixture is pH 9.5.

The resulting aqueous reaction mixture was then extracted EtOAc (4.0 L×2, 4 volumes×2) while agitating at 25° C. for 10 min, keeping the upper organic layer. The combined organic phase was then washed with water (4.0 L, 4 volumes) and subsequently concentrated in vacuo to a volume of 2–2.5 L. To the concentrated solution was added acetonitrile (4.0 L, 4 volumes) and concentrated in vacuo again until about 2 to 2.5 L (2 to 2.5 volumes) remained. Once again, to the concentrated solution was added acetonitrile (2.0 L, 2 volumes) and concentrate in vacuo until less than 2 L (<2 volumes) remains. The concentrated solution was removed from reduced pressure and agitated the at 45° C. until crystallization began. The resulting slurry was then cooled to a temperature of 0–5° C. over a period of 4–5 hr and held at said temperature for an additional 2 hrs prior to collecting, washing, and drying the crystalline form of the title compound. The typical yield for this two-step one pot process (Pd-catalyzed bridge formation and sugar cleavage) is 40–45%.

$^1$H (500 MHz, CDCl$_3$) δ 5.09, 4.98, 4.97, 4.78, 4.74, 4.43, 4.39, 4.07, 3.90, 3.84, 3.74, 3.67, 3.50, 3.43, 2.82, 2.79, 2.73, 2.62, 2.43, 2.31, 2.08, 2.03, 1.77, 1.59, 1.46, 1.38, 1.35, 1.32, 1.24, 1.23, 1.22, 1.22, 0.97, 0.97, 0.89

$^{13}$C (125 MHz, CDCl$_3$) δ 175.3, 170.2, 166.5, 143.7, 119.2, 99.7, 82.3, 79.5, 78.2, 78.1, 77.6, 77.3, 77.0, 76.1, 74.0, 71.7, 69.0, 65.6, 63.4, 43.9, 40.9, 37.5, 36.0, 34.3, 31.2, 25.7, 23.4, 21.7, 21.4, 20.0, 19.6, 17.11, 15.7, 14.8, 12.0, 7.9

Example 5

Preparation of 3-Decladinose-6,11-O,O-Bridged Erythromycin A 9-Imine Acetamide 2'-Acetate (Compound of formula (VI-b))

Step 5a.

Preparation of 3-Decladinose-6,11-O,O-Bridged Erythromycin A 9-Imine Acetamide 2'-Acetate (Compound of formula (V))

To an agitating solution of the title compound of Example 4 (1.00 kg) in ethanol (2 L, 2 volumes) was added 20% titanium (III) chloride solution in aqueous 3% hydrochloric acid (2.847 kg or 2.33 L) over the period of about 1 hr via an addition funnel, while adjusting the addition rate to control maintain the temperature between 25 to 35° C. After adding all of the titanium(III) chloride solution, the reaction mixture was then agitated for an additional 3 hrs at a temperature between 25° C. and 30° C. until the reaction was completed (by HPLC). To the reaction mixture was then added pre-chilled purified water (15 L, 15 volumes).

To the resulting aqueous reaction mixture was added a solution of sodium hydroxide (50%, w/w, 0.466 L) over a period of 0.5–1 hr, while adjusting the addition rate to maintain a temperature between 25 to 35° C., until the reaction mixture had reached a pH of between 6 to 7. The reaction mixture was then treated with saturated aqueous potassium carbonate solution (0.666 L) at 25 to 35° C. over a period of 1 to 2 hrs until the resulting reaction mixture was pH 9 to 10.

The basic aqueous reaction mixture was then extracted five times with methylene chloride (5.0 L×5, 5 volumes×5) and the combined organic extract is concentrated in vacuo until about 5 L remain. To the concentrated reaction mixture was then added additional methylene chloride (5.0 L) and removed in vacuo to azeotropically remove water until about 5 L remain. The resulting methylene chloride solution was directly used in the subsequent step without isolation.

Step 5b.

Preparation of the 9-Imine Acetate (Compound of formula (VI-b)).

Acetic anhydride (0.30 kg) is added to the concentrated solution from Step 5a and the resulting mixture was agitated at 25 to 30° C. for 1.5 hrs. After the acetylation reaction had gone to completion as evidenced by HPLC, the reaction mixture was concentrated in vacuo until approximately 2 L remained in the vessel. The remaining solution was then diluted with EtOAc (4.0 L, 4 volumes) and concentrated in vacuo until about 3 L remain. An additional amount of EtOAc (4.0 L, 4 volumes) was added to the concentrate and the diluted solution was concentrated once again in vacuo until crystallization began (about 1.5 L remaining). To the remaining slurry was added n-hexane (1.5 L, 1.5 volumes) while maintaining the temperature of the solution at about 45° C. After the addition of n-hexanes was complete, cool the solution to 0 to 5° C. over the period of about 3 hr and agitate the resulting slurry at this temperature for at least 2 hr before filtration. The crystals were then filtered and washed with chilled (<5° C.) ethyl acetate/hexane (1:2) (0.3 L, 0.3 volume). The collected crystals of the title compound were then dried under a vacuum at a temperature of about 40–45° C. until a constant weight was observed. The typical yield for this two-step one pot process (reduction and acetylation) is 80–89%.

$^1$H (500 MHz, CDCl$_3$) δ 5.18, 4.93, 4.75, 4.74, 4.59, 4.52, 4.13, 1.08, 3.74, 3.60, 3.48, 3.43, 2.84, 2.73, 2.72, 2.66, 2.55, 2.43, 2.26, 2.02, 1.73, 1.69, 1.46, 1.39, 1.33, 1.31, 1.26, 1.23, 1.23, 1.23, 1.10, 0.97, 0.91

$^{13}$C (125 MHz, CDCl$_3$) δ 184.9, 178.0, 174.9, 170.1, 142.1, 122.4, 99.8, 81.6, 79.1, 78.2, 77.5, 77.3, 77.0, 76.3, 76.2, 73.8, 71.9, 69.1, 65.9, 63.4, 43.8, 40.9, 40.0, 38.4, 36.3, 35.7, 31.1, 25.7, 23.3, 21.7, 21.4, 20.0, 19.7, 17.2, 16.0, 14.7, 12.0, 7.9

Example 6

Preparation of 6,11-O,O-Bridged Ketone Erythromycin A 9-Imine Acetamide 2'-Acetate 3-ketolide (compound of formula (VIII-b))

Step 6a.

Preparation of 3-Descladinose-6,11-Bridged Ketone Erythromycin A 9-Imine Acetamide 2'-Acetate (Compound of formula VII-b)

To an agitating solution of the title compound of Example 5 (1.00 kg) in acetone (1.75 L, 1.75 volumes) was added sodium periodate (s, 0.662 kg) and purified water (3.5 L, 3.5 volumes), cooling the resulting reaction mixture to a temperature of 15° C. While allowing the reaction mixture to warm, a 4% by weight solution of osmium tetroxide in water (87 ml) was added gradually over a period of 10 min (exothermic addition, temperature rises approximately 35° C. After the addition of the osmium tetroxide solution was complete, the reaction mixture was agitated at 25°–35° C. for a period of 2 hrs or until the reaction has gone to completion as evidenced by HPLC and MS. If the diol intermediate persists, then add an additional 10% sodium periodate (0.066 kg) and agitate for an additional 1 hr. The reaction mixture was then diluted with EtOAc (10 L. 10 volumes) and treated with saturated aqueous sodium bicarbonate (4 L, 4 volumes). The organic phase was separated and the remaining aqueous solution was extracted an additional two times with EtOAc (4 L, 4 volumes). To the combined organic extracts was added over a period of 15 min to an aqueous solution of sodium metabisulfite (0.7 kg in 1.5 L (1.5 volumes)) and saturated sodium bicarbonate solution (4L, 4 volumes) to quench any remaining oxidizing reagent. The resulting solution was then washed 15% aqueous sodium chloride solution (5 L, 5 volumes). The remaining organic phase was then concentrated in vacuo at a temperature of about 50° C. until approximately 2 L remain. To ensure that all water was eliminated from the solution, toluene (5 L, 5 volumes) was added and the resulting solution was concentrated in vacuo until approximately 2 L remain in order to azeotropically remove any remaining water. The resulting concentrated solution was then diluted with methylene chloride (5 L, 5 volumes) and concentrated once again in vacuo at 50° C. until 3.5 L remain. The resulting methylene chloride/toluene solution was used in the subsequent step without isolation.

Step 6b. Corey-Kim Reaction to Prepare the Title Compound of Formula (VIII-b).

A solution of N-chlorosuccinimide (NCS) (0.197 kg) in methylene chloride (3.5 L, 3.5 volumes) was agitated and cooled to a temperature of approximately −15° C. To the cooled solution was added dimethyl sulfide (0.145 L) over a period of 30 min via an addition funnel while controlling the reaction temperature to about −15° C. After maintaining a temperature of −15° C. for 15 min., the solution was further cooled to a temperature of approximately −20° C. and to this cooled solution was added the methylene chloride/toluene solution of the olefin cleavage intermediate solution prepared in Step 6a while maintaining a reaction temperature of approximately −20° C. The reaction mixture was agitated for an additional 3 hrs at a temperature of approximately −20° C., after which triethylamine (TEA) (0.196 L) was gradually added over a period of about 30 min. During the addition of TEA, the reaction mixture was maintained at −15° C. by controlling the rate of addition. The resulting reaction mixture was then agitated at the temperature of −15° C. for an additional 1 hr, after which the reaction mixture was warmed to 10° C. and diluted with EtOAc (16 L, 16 volumes). The diluted reaction mixture was then washed with saturated aqueous sodium bicarbonate solution (5 L×2, 5 volumes) and half-saturated aqueous sodium chloride solution (5 L, 5 volumes). The remaining organic solution was then concentrated in vacuo at a temperature range of 45° C. to 50° C. until 1.5 L remain. To the concentrated solution is added ethanol (2.5 L, 2.5 volumes) while continuing to concentrate the organic solution in vacuo until crystallization begins. The concentrated solution was then cooled gradually to a temperature of 0° C. for a period of at least 2 hrs. The crystalline title compound was then collected, washed with chilled (about 0° C.) ethanol (0.15 L), and dried at 25° C. under reduced pressure. The typical yield for this two-step one pot process (oxidative cleavage and Corey-Kim oxidation) is 55–60%.

$^1$H (500 MHz, CDCl$_3$) δ 4.93, 4.78, 4.63, 4.53, 4.41, 4.34, 4.24, 4.00, 3.95, 3.65, 3.56, 3.44, 2.87, 2.83, 2.67, 2.64, 2.36, 2.08, 2.07, 1.84, 1.79, 1.57, 1.49, 1.38, 1.35, 1.33, 1.32, 1.29, 1.28, 1.27, 1.17, 0.92

$^{13}$C (125 MHz, CDCl$_3$) δ 205.5, 205.2, 184.5, 175.8, 170.2, 169.7, 100.0, 80.2, 79.0, 78.9, 77.6, 76.1, 75.8, 74.6, 71.6, 69.3, 68.7, 63.5, 58.4, 51.0, 45.4, 40.8, 39.7, 38.7, 36.6, 30.8, 25.5, 23.1, 21.6, 21.2, 20.0, 19.6, 18.6, 17.2, 15.5, 14.2, 13.0, 11.6

Example 7

Preparation of O-(6-Pyrazol-1-yl-pyridin-3-ylmethyl)-hydroxylamine (Compound of formula (XI))

Step 7a.

Preparation of 6-Pyrazol-1-yl-nicotinic acid methyl ester (Compound of formula (XI-a))

To a solution of pyrazole (19.4 g, 0.28 mol) in 100 mL anhydrous DMSO, which was at a temperature of 0° C., was added NaH (7.5 g, 0.3 mol) gradually over a period of 30 min. The resulting reaction mixture was allowed to warm to room temperature, at which the mixture continued to agitate for an additional 30 min. Methyl 6-chloronicotinate (35 g, 0.2 mol) was added to the stirring reaction mixture and agitated vigorously for a period of 6 hr. The reaction mixture was subsequently cooled to a temperature of about 0° C. and poured into a saturated aqueous, 0° C. NH$_4$Cl solution. The resulting precipitate was filtered, washed with water, and dried to give a compound of formula (XI-a) (38.3 g, 93% yield) as an off-white solid.

Step 7b. Preparation of (6-Pyrazol-1-yl-pyridin-3-yl)-methanol (Compound of formula (XI-b))

A mixture of the title compound of step 8a (23.5 g, 0.116 mol), NaBH$_4$ (8.0 g, 0.232 mol) in 250 ml tBuOH was heated to reflux. While refluxing, to the reaction mixture was added methanol (50 ml) gradually over the period of 1 hr. The resulting reaction mixture was stirred under reflux conditions for an additional 5 hrs and subsequently quenched with 2N HCl. The solvent was removed in vacuo, the residue was diluted with ethyl acetate, and washed with saturated NaHCO$_3$ and brine. The remaining organic solution was then dried over Na$_2$SO$_4$ and concentrated. The residue was recrystallized from hexanes to afford the compound of formula (XI-b) (18 g, 90% yield) as a yellow solid.

Step 7c. Preparation of 5-Chloromethyl-2-pyrazol-1-yl-pyridine (Compound of formula (XI-c)

To a solution of alcohol 4 (10.5 g, 59.9 mmol) in CH$_2$Cl$_2$ (150 ml), SOCl$_2$ (36 g, 22 ml, 299.6 mmol) was added and the resulting reaction mixture was stirred at room temperature for a period of between 12 to 18 hours. The excess SOCl$_2$ was quenched with saturated aqueous NaHCO$_3$. The resulting mixture was extracted with CH$_2$Cl$_2$ and washed with brine. Removal of solvent gave a compound of formula (XI-c) (11.15 g, 95% yield) as a white solid.

Step 7d. Preparation of 2-(6-Pyrazol-1-yl-pyridin-3-yl-methoxy)-isoindole-1,3-dione (Compound of formula (XI-d))

To a solution of N-hydroxyphthalimide 6 (19.2 g, 115.2 mmol) in anhydrous DMF (80 ml) is added NaH (3.12 g, 0.13 mol) and the resulting reaction mixture was stirred for 0.5 hr. The compound of Step 8c (11.15 g, 57.6 mmol) was added and the resulting mixture was stirred and heated to a temperature of 40–50° C. for a period of 3 h. The reaction mixture was then allowed to cool to a temperature of approximately 25° C. and subsequently quenched with cold water prior to filtering the quenched solution. The precipitate was washed with cool water, dried, and redissolved in a mixture of ethyl acetate and CH$_2$Cl$_2$. The solution was subsequently washed with brine, concentrated in vacuo to yield a yellow solid in quantitative yield.

Step 7e. Preparation of the Title Compound of Formula (XI)

A solution of the compound of Step 7d (32 g, 0.1 mol) in 100 ml of 2M NH$_3$ in methanol was stirred at 50° C. for 4 hours. The reaction mixture was subsequently concentrated in vacuo and purified on silica gel to give the desired compound of formula (XI) (18.5 g, 97%).

Example 8

Preparation of Compound of Formula (IX-b)

Step 8a.

Addition of O-(6-Pyrazol-1-yl-pyridin-3-ylmethyl)-hydroxylamine (compound of formula (XI))

To an agitated solution of the O-(6-Pyrazol-1-yl-pyridin-3-ylmethyl)-hydroxylamine (compound of formula (XI))

(0.32 kg) prepared in Example 7 in ethanol (2.76 L, 2.76 volumes) was added 1 M aqueous hydrochloric acid (2.76 L, 2.76 volumes) while maintaining a temperature below 25° C. by controlling the rate of addition. The resulting reaction mixture was then cooled to a temperature between 0 to 4° C. To the cooled reaction mixture is added the title compound of Example 7 (1.00 kg) while maintaining a reaction temperature less than 5° C. After the addition had been completed, the reaction mixture was agitated for a period of 1 to 2 hrs while allowing to warm to 23° C. The reaction mixture was subsequently diluted with EtOAc (7 L, 7 volumes) and to this diluted reaction mixture was added saturated aqueous sodium bicarbonate solution (6.0 L, 6 volumes) at a temperature below 25° C. until the pH of the mixture was between 8 and 9. Agitate the resulting aqueous solution at 23° C. for 10 min retaining the organic layer and extracting the aqueous phase with additional EtOAc (4.0 L, 4 volumes). The combined organic extract is then concentrated in vacuo until only a sticky oil residue remains. This residue was used in the subsequent step without isolation.

Step 8b.

2' Deprotection

To the residue was added methanol (5.0 L, 5 volumes) and was concentrated in vacuo azeotropically removing any remaining water until 2 L remain. This remaining solution then underwent polishing filtration and was subsequently agitated for a period of 15 hrs at a temperature of 20–23° C., after which the deacetlyation reaction was complete as evidenced by HPLC. The reaction mixture was then concentrated in vacuo until approximately 1.5 L remains. The residue was then diluted with ethanol (5.0 L, 5 volumes) and concentrated until approximately 3.5 L remain. To this residue was added purified water while maintaining a vacuum and a temperature of approximately 80° C. The vacuum was released and the aqueous solution was further agitated at 75° C. while allowing to cool to a temperature of approximately 20° C. over a period of 3 hrs. Once the solution had reached a temperature of 20° C., the aqueous slurry was agitated for an additional period of 2 hrs and subsequently filtered. The filtered material was washed with chilled (less than 5° C.) (1:2) ethanol/water (0.3 L, 0.3 volumes) while retaining the mother liquor and washing solution for future use. After drying the crystalline material, it was dissolved once again in ethanol and recrystallized in the same manner as previously described to arrive upon the title compound. The typical yield for this three-step one pot process (oxime formation, 2' deprotection, and recrystallization) is 55%.

$^1$H (500 MHz, CDCl$_3$) δ 8.58, 8.42, 7.93, 7.85, 7.75, 6.47, 5.31, 4.72, 4.64, 4.63, 4.51, 4.47, 4.35, 3.99, 3.98, 3.61, 3.55, 3.46, 3.18, 2.80, 2.75, 2.62, 2.49, 2.28, 2.01, 1.81, 1.69, 1.68, 1.46, 1.41, 1.38, 1.33, 1.33, 1.29, 1.26, 1.16, 1.00

$^{13}$C (125 MHz, CDCl$^3$) δ 205.8, 184.7, 177.9, 167.8, 154.0, 151.3, 148.1, 142.2, 139.2, 131.3, 127.2, 112.1, 107.9, 103.1, 79.3, 79.2, 77.6, 77.4, 77.1, 76.7, 74.6, 73.1, 70.5, 69.7, 66.0, 63.1, 62.7, 50.7, 46.2, 40.4, 38.7, 28.5, 25.3, 23.8, 21.5, 20.2, 19.5, 17.8, 15.0, 14.1, 13.7, 13.0

Although the invention has been described in detail with respect to various preferred embodiments it is not intended to be limited thereto, but rather those skilled in the art will recognize that variations and modifications may be made therein which are within the spirit of the invention and the scope of the appended claims.

What is claimed:

1. A process comprising the step of reacting a compound of formula (I):

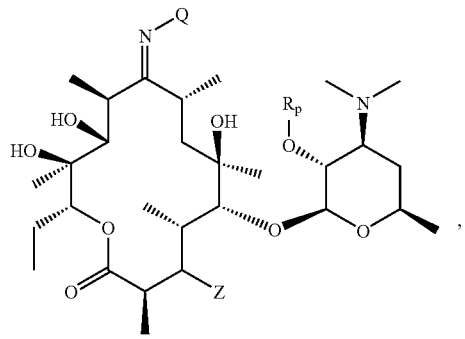

or a pharmaceutically acceptable salt thereof, with a compound of formula II:

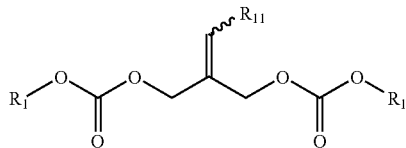

to produce a compound of formula III:

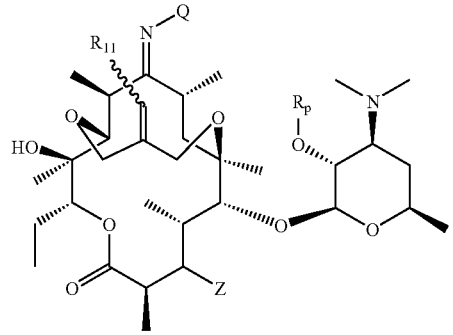

wherein,

Each $R_1$ is independently hydrogen, acyl, silane, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group;

Each of $R_3$ and $R_4$ is independently hydrogen, acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, saturated or unsaturated heterocyclic group; or can be taken together with the nitrogen atom to which they are attached to form a substituted or unsubstituted heterocyclic or heteroaromatic ring;

Q is independently $R_1$, $OR_1$, or $OC(O)R_1$;

Z is $R_1$, $OR_1$, $OC(O)R_1$, $OC(O)NR_3R_4$, $OS(O)_nR_1$, or

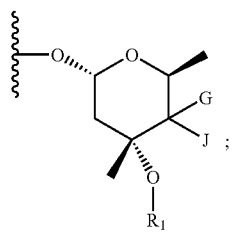

one of J or G is hydrogen and the other is $R_1$, $OR_1$, or $NR_3R_4$;

or, J and G, taken together with the carbon atom to which they are attached, are C=O, C=NR$_1$, C=NOR$_1$, C=NO(CH$_2$)$_m$R$_1$, C=NNHR$_1$, C=NNHCOR$_1$, C=NNHCONR$_3$R$_4$, C=NNHS(O)$_n$R$_1$, or C=N—N=CHR$_1$;

$R_{11}$ is independently $R_1$;

$R_p$ is independently $R_1$;

m is an integer between 1 and about 24; and n is 0, 1, or 2.

2. The process of claim 1, wherein the step of reacting occurs in the presence of a palladium catalyst.

3. The process of claim 2, wherein the palladium catalyst is a palladium (0) catalyst.

4. The process of claim 2, wherein the palladium catalyst is (dibenzylideneacetone)dipalladium [Pd$_2$(dba)$_3$].

5. The process of claim 1, wherein the step of reacting is in the presence of a monodentate phosphorous-containing ligand.

6. The process of claim 1, wherein the step of reacting is in the presence of a bidentate phosphorous-containing ligand.

7. The process of claim 1, wherein the step of reacting is in the presence of 1,4-bis(diphenylphosphino)butane.

8. The process of claim 1, wherein the step of reacting occurs in an aprotic solvent.

9. The process of claim 8, wherein the aprotic solvent is tetrahydrofuran.

10. The process of claim 1, wherein for formula I, Q is OAc, $R_p$ is Ac, and Z is

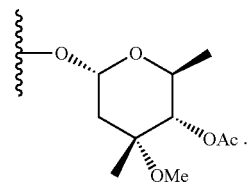

11. The process of claim 1, wherein for formula II, $R_{11}$ is hydrogen and $R_1$ is tert-butyl.

12. The process of claim 1, wherein for formula III, $R_{11}$ is hydrogen, Q is OAc, $R_p$ is Ac, and Z is

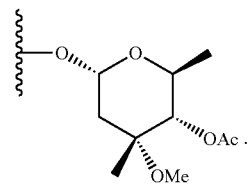

13. The process of claim 1, further comprising the steps of:

(a) hydrolyzing a compound of formula (III) with a mild acid to provide a compound of formula (IV-a):

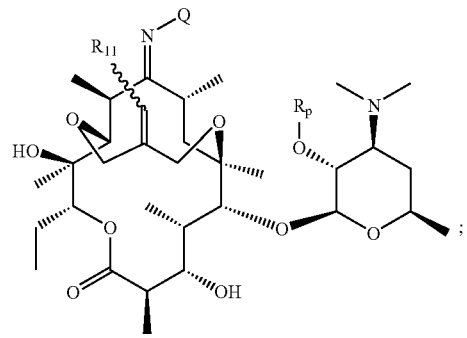

(b) reducing a compound of formula (IV-a) with a reducing agent to provide a compound of formula (V):

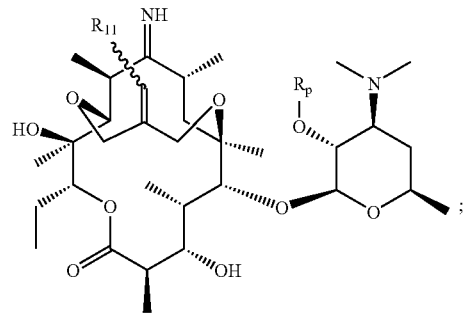

(c) acylating a compound of formula (V) with an acylating agent to provide a compound of formula (VI-a):

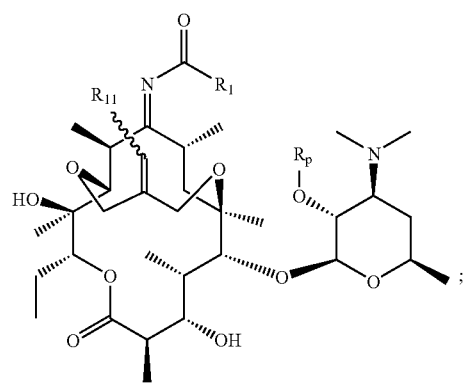

(d) oxidatively cleaving a compound of formula (VI-a) with a cleaving reagent or reagents to provide a compound of formula (VII-a):

[chemical structure]

(e) oxidizing a compound of formula (VII-a) with an oxidizing agent or agents to provide a compound of formula (VIII-a):

[chemical structure]

and (f) reacting a compound of formula (VIII-a) with a compound of formula (X):

$R_1$—O—$NH_2$ in the presence of an acid or base to provide a compound of formula (IX-a):

[chemical structure]

14. The process of claim 13, wherein the steps of reacting and hydrolyzing are carried out in a one pot process.

15. The process of claim 13, wherein the steps of reducing and acylating are carried out in a one pot process.

16. The process of claim 13, wherein the steps of oxidatively cleaving and oxidizing are carried out in a one pot process.

17. The process of claim 13, wherein for the step of hydrolyzing, the mild acid is hydrochloric acid, sulfuric acid, chloroacetic acid, dichloroacetic acid, or trifluoroacetic acid.

18. The process of claim 13, wherein for the step of hydrolyzing, the mild acid is aqueous hydrochloric acid.

19. The process of claim 13, wherein the step of hydrolyzing occurs in a protogenic solvent.

20. The process of claim 19, wherein the protogenic solvent is water, methanol, ethanol, isopropanol, or butanol.

21. The process of claim 19, wherein the protogenic solvent is water.

22. The process of claim 13, wherein for formula IV, Q is hydroxy, $R_{11}$ is hydrogen, and $R_p$ is Ac.

23. The process of claim 13, wherein for the step of reducing, the reducing agent is lithium aluminum hydride, titanium(III)chloride, borane, hydrogen sulfide, or sodium nitrite.

24. The process of claim 13, wherein for the step of reducing, the reducing agent is a titanium (III) reducing agent.

25. The process of claim 24, wherein for the step of reducing, the titanium (III) reducing agent is titanium(III) chloride.

26. The process of claim 13, wherein the step of reducing occurs in a protogenic solvent.

27. The process of claim 26, wherein the protogenic solvent is water, methanol, ethanol, isopropanol, butanol, or mixtures thereof.

28. The process of claim 26, wherein the protogenic solvent is ethanol.

29. The process of claim 13, wherein the step of reducing occurs in the presence of an acid.

30. The process of claim 29, wherein the acid is acetic acid, formic acid, dilute hydrochloric acid, dilute phosphoric acid, or dilute sulfuric acid.

31. The process of claim 29, wherein the acid is aqueous hydrochloric acid.

32. The process of claim 13, wherein for formula V, $R_{11}$ is hydrogen and $R_p$ is Ac.

33. The process of claim 13, wherein for the step of acylating, the acylating agent is acetyl chloride, acetic anhydride, benzoyl chloride, benzoic anhydride, or benzyl chloroformate.

34. The process of claim 13, wherein the acylating agent is acetic anhydride.

35. The process of claim 13, wherein the step of acylating occurs in an aprotic solvent.

36. The process of claim 35, wherein the aprotic solvent is dichloromethane, chloroform, N,N-dimethylformamide, tetrahydrofuran, N-methylpyrrolidinone, or mixtures thereof.

37. The process of claim 35, wherein the aprotic solvent is dichloromethane.

38. The process of claim 13, wherein for formula VI-a, Q is Ac, $R_{11}$ is hydrogen, and $R_p$ is Ac.

39. The process of claim 13, wherein for the step of oxidatively cleaving, the oxidative cleavage reagents are an oxidant and a cleaving reagent.

40. The process of claim 39, wherein the oxidant is permanganate or ion osmium tetroxide.

41. The process of claim 39, wherein the oxidant is osmium tetroxide.

42. The process of claim 39, wherein the cleaving reagent is periodic acid, lead tetraacetate, manganese dioxide, potassium permanganate, sodium periodate, sodium metaperiodate, or N-iodosuccinamide.

43. The process of claim 39, wherein the cleaving reagent is sodium periodate.

44. The process of claim 39, wherein the step of oxidatively cleaving occurs in a solvent mixture is a mixture of water and one of the following solvents: 1,4-dioxane, tetrahydrofuran, tert-butanol, acetone, or diethyl ether.

45. The process of claim 44, wherein the solvent mixture is water in acetone.

46. The process of claim 13, wherein for formula VII-a, $R_1$ is methyl and $R_p$ is Ac.

47. The process of claim 13, wherein for the step of oxidizing, the oxidizing agents is a chromium(VI) reagent, Swern reagent, or Corey-Kim reagent.

48. The process of claim 13, wherein the step of oxidizing occurs in an aprotic solvent.

49. The process of claim 48, wherein the aprotic solvent is methylene chloride.

50. The process of claim 13, wherein for formula VIII-a, $R_1$ is methyl and $R_p$ is Ac.

51. The process of claim 13, wherein for the step of reacting, the acid is hydrochloric acid, phosphoric acid, caomphorsulfonic acid, sulfuric acid, para-toluenesulfonic acid, or pyridinium para-toluene sulfonate.

52. The process of claim 13, wherein for the step of reacting, the acid is aqueous hydrochloric acid.

53. The process of claim 13, wherein the step of reacting occurs in a protogenic solvent.

54. The process of claim 53, wherein the protogenic solvent is ethanol.

55. The process of claim 13, wherein for the formula (X), $R_1$ is pyridyl-pyrazolyl.

56. The process of claim 13, wherein for the formula (IX-a), $R_1$ is pyridyl-pyrazolyl.

* * * * *